United States Patent
Nakayama et al.

(10) Patent No.: US 9,057,682 B2
(45) Date of Patent: Jun. 16, 2015

(54) BLADE VIBRATION MEASURING APPARATUS

(75) Inventors: Kohichi Nakayama, Yokohama (JP); Kenji Osaki, Yokohama (JP); Hisashi Matsuda, Tokyo (JP); Hitoshi Sakakida, Tokyo (JP); Toshio Hirano, Yokohama (JP); Toshiaki Hirate, Kawasaki (JP); Sueyoshi Mizuno, Tokyo (JP); Ikuo Saito, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 356 days.

(21) Appl. No.: 13/613,398

(22) Filed: Sep. 13, 2012

(65) Prior Publication Data

US 2013/0247671 A1    Sep. 26, 2013

(30) Foreign Application Priority Data

Sep. 13, 2011  (JP) ................................ 2011-199452
Oct. 11, 2011  (JP) ................................ 2011-224050

(51) Int. Cl.
*G01N 29/12*  (2006.01)
*G01N 29/04*  (2006.01)
(Continued)

(52) U.S. Cl.
CPC  *G01N 29/12* (2013.01); *F01D 5/16* (2013.01); *F01D 21/003* (2013.01); *F05D 2220/31* (2013.01); *G01H 3/04* (2013.01); *G01H 3/10* (2013.01)

(58) Field of Classification Search
USPC .................. 73/579, 593, 602, 655, 659, 660; 702/56, 76, 179, 187
See application file for complete search history.

(56) References Cited

U.S. PATENT DOCUMENTS 3,929,008 A * 12/1975 Zlotin et al. .................... 73/660
5,511,426 A *  4/1996 Clement et al. ................ 73/655
(Continued)

FOREIGN PATENT DOCUMENTS

JP    S62-285028 A    12/1987
JP    11-030551         2/1991
(Continued)

OTHER PUBLICATIONS

Japanese Office Action mailed Nov. 4, 2014 in corresponding Japanese Application No. 2011-199452 (with English translation).
(Continued)

*Primary Examiner* — Helen Kwok
(74) *Attorney, Agent, or Firm* — Harness, Dickey & Pierce, PLC

(57) ABSTRACT

According to the embodiment, there is provided a blade vibration measuring apparatus, having, a contactless displacement sensor which outputs a displacement measurement signal as measuring a displacement of a turbine moving blade in a rotation axis direction, a blade top position identifying device which outputs a blade top position identification signal to identify a top position based on a distance between the contactless displacement sensor and the top position of the turbine moving blade as receiving the displacement measurement signal output from the contactless displacement sensor, and a blade vibration calculating device which calculates vibration amplitude and a vibration frequency of the turbine moving blade based on temporal variation of the distance between the contactless displacement sensor and the top position of the turbine moving blade as receiving the blade top position identification signal output from the blade top position identifying device.

15 Claims, 29 Drawing Sheets

(51) Int. Cl.
 *G01N 29/00* (2006.01)
 *F01D 5/16* (2006.01)
 *F01D 21/00* (2006.01)
 *G01H 3/04* (2006.01)
 *G01H 3/10* (2006.01)

(56) References Cited

U.S. PATENT DOCUMENTS

| | | | |
|---|---|---|---|
| 7,168,324 B2 * | 1/2007 | Boda et al. | 73/660 |
| 2002/0162394 A1 * | 11/2002 | Loftus et al. | 73/593 |
| 2006/0000283 A1 * | 1/2006 | Twerdochlib | 73/593 |
| 2010/0030493 A1 * | 2/2010 | Rao | 702/39 |
| 2010/0089166 A1 * | 4/2010 | Zielinski et al. | 73/660 |
| 2010/0153031 A1 * | 6/2010 | Russhard | 702/56 |
| 2010/0171491 A1 | 7/2010 | Chana | |
| 2010/0179775 A1 * | 7/2010 | Loftus | 702/56 |

FOREIGN PATENT DOCUMENTS

| | | |
|---|---|---|
| JP | H07-027601 A | 1/1995 |
| JP | H07-063606 A | 3/1995 |
| JP | H08-082547 A | 3/1996 |
| JP | 10-068654 A | 3/1998 |
| JP | H10-148568 A | 6/1998 |
| JP | 2000-321122 A | 11/2000 |
| JP | 2002-098584 | 4/2002 |
| JP | 2003-177059 A | 6/2003 |
| JP | 2010-531954 A | 9/2010 |
| WO | WO2009/004319 | 1/2009 |

OTHER PUBLICATIONS

Japanese Office Action issued on Nov. 4, 2014 in corresponding Japanese Application No. 2011-224050 (with English translation).

* cited by examiner

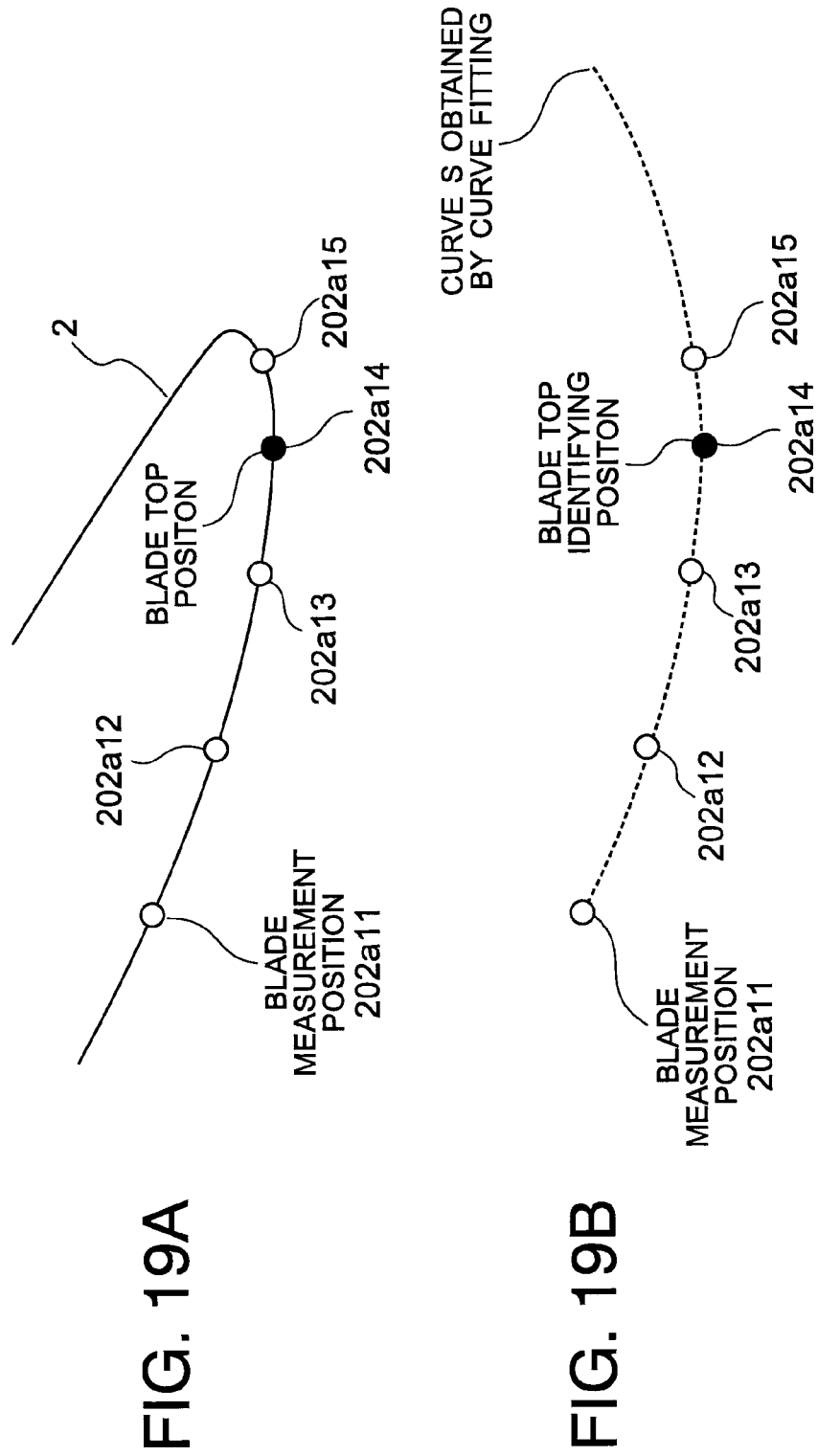

BLADE VIBRATION MEASURING APPARATUS

CROSS REFERENCE TO RELATED APPLICATION

This application is based upon and claims benefit of priority under 35 USC 119 from the Japanese Patent Application No. 2011-199452, filed on Sep. 13, 2011, and the Japanese Patent Application No. 2011-224050, filed on Oct. 11, 2011, the entire contents of which are incorporated herein by reference.

FIELD

The present invention relates to a blade vibration measuring apparatus for measuring vibration occurring at a moving blade of a variety of turbines and the like.

BACKGROUND

In design developing and manufacturing of a variety of turbines such as a steam turbine and a gas turbine, it is required to measure vibration occurring at a turbine moving blade for ensuring reliability as preventing an accident as well as improving performance.

A conventional apparatus to measure blade vibration adopts a method to measure blade passing timing by using a proximity sensor and to obtain vibration based on time difference of the passing timing.

With the conventional blade vibration measuring apparatus, it is required to accurately measure the blade passing timing at a high sampling frequency being several hundred MHz or higher. Accordingly, it is required to prepare a data acquisition device which has a high sampling frequency and high time resolution capability.

Further, to obtain high time measurement accuracy, attentiveness is necessary not only for performance of the acquisition device but also for transmission time of a measurement signal. In addition, measured phase difference (time difference) is required to be converted into a displacement. Accordingly, there is a problem that much time and cost are required for measurement preparation and measured data analysis.

On the other hand, there is a method to directly measure blade vibration by using a contactless displacement sensor instead of a proximity sensor.

With this method, since measurement is performed at a sampling frequency on the order of several hundred kHz, time resolution capability required for a data acquisition device is relatively low and preparation of a measurement system and data analysis are relatively easy.

However, when a large-sized rotational blade such as a final-stage blade of a steam turbine or the like is to be measured, displacements at a constant position cannot be captured owing to sampling incapability to catch up blade revolution speed. Accordingly, it is difficult to perform measurement of blade vibration at high accuracy.

BRIEF DESCRIPTION OF THE DRAWINGS

FIGS. 19A and 19B are explanatory views indicating a method to perform curve fitting on a plurality of measurement points of an output signal of a contactless displacement sensor according to the eleventh embodiment;

DETAILED DESCRIPTION

Embodiments will now be explained with reference to the accompanying drawings.

According to the present invention, there is provided a blade vibration measuring apparatus, comprising:

a contactless displacement sensor which outputs a displacement measurement signal as measuring a displacement of a turbine moving blade in a rotation axis direction;

a blade top position identifying device which outputs a blade top position identification signal to identify a top position based on a distance between the contactless displacement sensor and the top position of the turbine moving blade as receiving the displacement measurement signal output from the contactless displacement sensor; and a blade vibration calculating device which calculates vibration amplitude and a vibration frequency of the turbine moving blade based on temporal variation of the distance between the contactless displacement sensor and the top position of the turbine moving blade as receiving the blade top position identification signal output from the blade top position identifying device.

In the following, blade vibration measuring apparatuses according to embodiments of the present invention will be described with reference to the drawings.

(First Embodiment)

Figure 1:
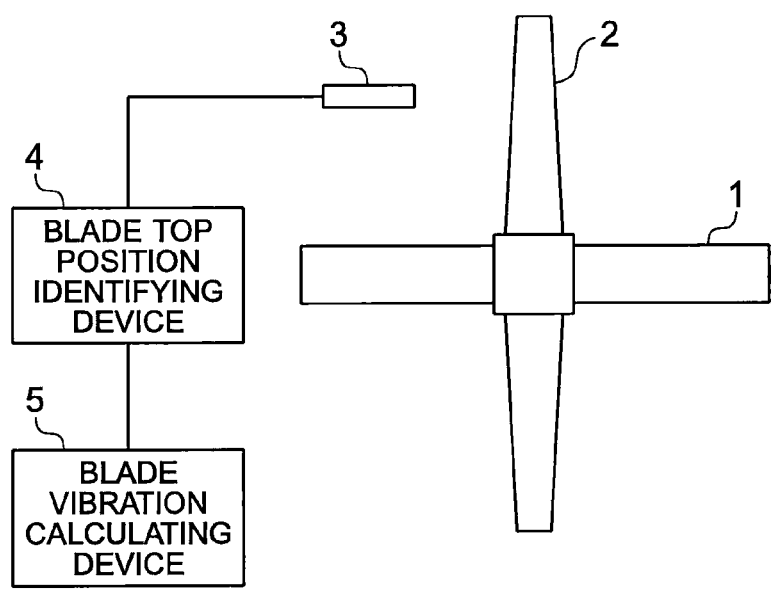
FIG. 1 is an explanatory view illustrating arrangement and a block structure of a blade vibration measuring apparatus according to a first embodiment.

FIG. 1 illustrates a structure of a blade vibration measuring apparatus according to a first embodiment of the present invention.

The apparatus is provided with a contactless displacement sensor 3, a blade top position identifying device 4, and a blade vibration calculating device 5.

The contactless displacement sensor 3 is solely attached as being close to a turbine moving blade 2 in a direction of being in parallel to a rotary shaft 1 and outputs a displacement measurement signal as directly measuring a displacement in the rotation axis direction of the turbine moving blade 2 which is rotated in a direction being perpendicular to a paper face of the drawing.

The blade top position identifying device 4 receives the displacement measurement signal output from the contactless displacement sensor 3 and outputs a blade top position identification signal which indicates an identification result through performing identification of a blade top position.

The blade vibration calculating device 5 calculates vibration amplitude and a vibration frequency of the turbine moving blade 2 as receiving the blade top position identification signal.

Figure 2A:
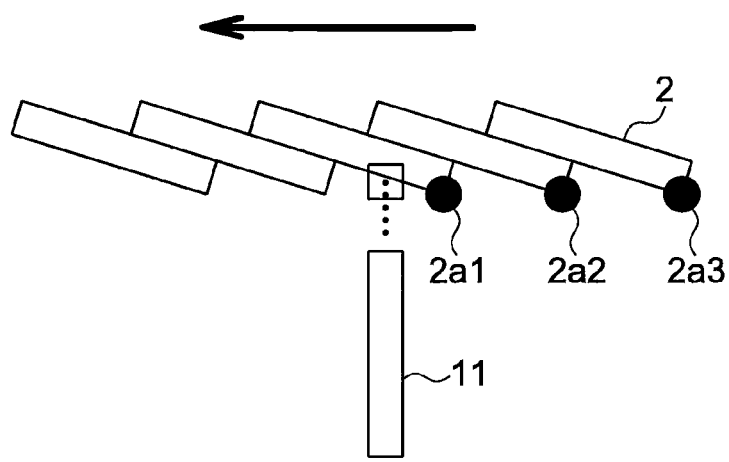
FIGS. 2A and 2B are an explanatory view of a blade top position identifying method with the blade vibration measuring apparatus according to the first embodiment and a graph indicating temporal variation of an output voltage waveform from a contactless displacement sensor.
Figure 2B:
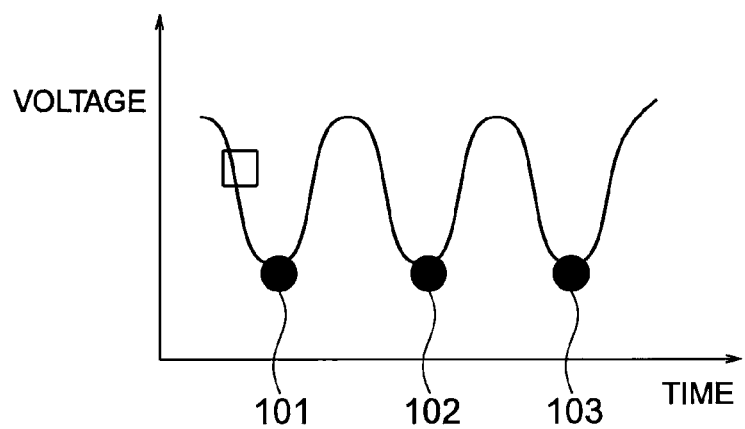

Description will be performed by using FIGS. 2A and 2B on procedure to identify the top position of the turbine moving blade 2 in a case that an eddy current displacement sensor 11 is used as the contactless displacement sensor 3.

Owing to that a blade row of the turbine moving blade 2 passes through the front of the eddy current displacement sensor 11 as being rotated and moved in a direction indicated by an arrow as illustrated in FIG. 2A, it is possible to obtain an output voltage waveform as illustrated in FIG. 2B from the eddy current displacement sensor 11. Here, a detection position of the turbine moving blade 2 by the eddy current displacement sensor 11 indicated by a square in FIG. 2A corresponds to a position indicated by a square on the output voltage waveform in FIG. 2B.

Further, top positions of the turbine moving blade 2 indicated by dots 2a1, 2a2, 2a3 in FIG. 2A correspond to lowermost peak values of the output voltage waveform indicated by dots 101, 102, 103 in FIG. 2B.

The blade top position identifying device 4 performs identification of the blade top position from the peak value of the output voltage waveform provided from the eddy current displacement sensor 11 and outputs the blade top position identification signal to provide to the blade vibration calculating device 5.

A method of blade vibration calculation with the blade 15 vibration calculating device 5 will be described by using FIGS. 3A and 3B.

Figure 3A:
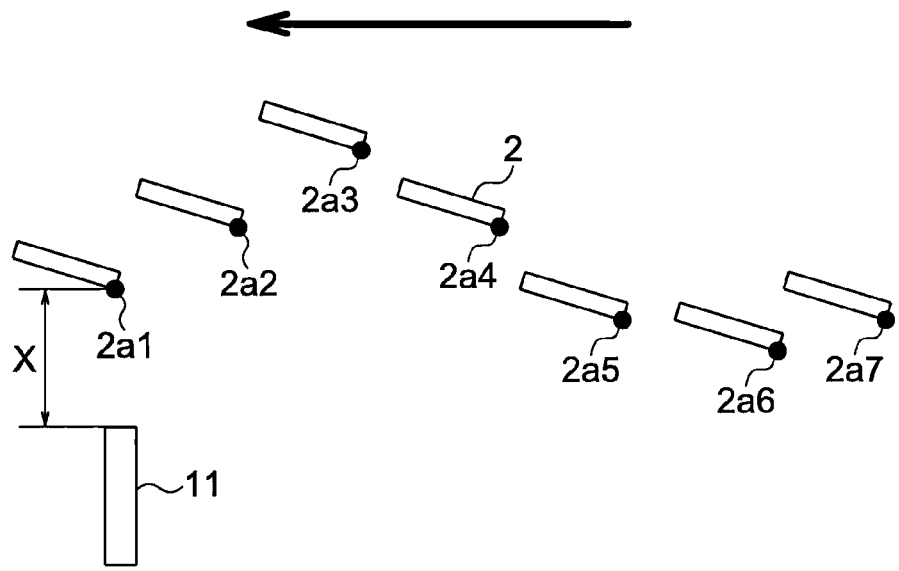
FIGS. 3A and 3B are an explanatory view and a graph illustrating distance variation between top positions of a turbine moving blade and the contactless displacement sensor of the blade vibration measuring apparatus according to the first embodiment.
Figure 3B:
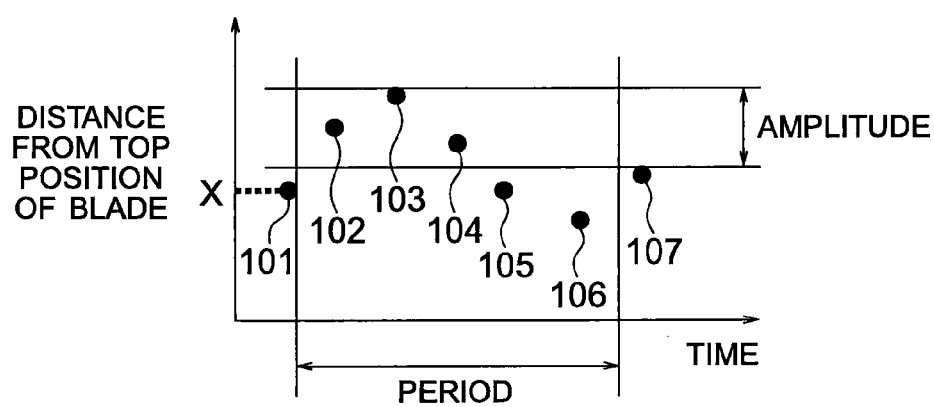

As illustrated in FIG. 3A, when vibration occurs at the turbine moving blade 2, the distance X from the top positions of the turbine moving blade 2 indicated by dots 2a1, 2a2, 2a3, 2a4, 2a5, 2a6, 2a7 to the eddy current displacement sensor 11 is fluctuated. This fluctuation becomes the fluctuation of the lowermost peak value of the output voltage waveform indicated by the dots 101, 102, 103, 104, 105, 106, 107 described by using FIG. 2B. Accordingly, the voltage corresponding to the blade top position output from the blade top position identifying device 4 is converted into a relative distance between the blade top position and the eddy current displacement sensor 11 at the blade vibration calculating device 5 and the obtained relative distance is recorded in chronological order as illustrated in FIG. 3B. The vibration 30 amplitude and the vibration frequency of the turbine moving blade 2 can be calculated from the chronological data recorded as described above.

According to the first embodiment, time and cost required for the measurement can be reduced by directly measuring the displacement of the turbine moving blade in the rotation axis direction with the eddy current displacement sensor.

In the first embodiment, the eddy current displacement sensor 11 is used as an example of the contactless displacement sensor 3. Here, not limited to the above, it is only required to be capable of measuring a displacement to the turbine moving blade 2 in a contactless manner. For example, an optical fiber or the like may be used. In a case that an optical fiber is used, being contrary to an eddy current displacement sensor, there appears a relation that output becomes larger with decrease of the distance to the turbine moving blade.

(Second Embodiment)

Figure 4:
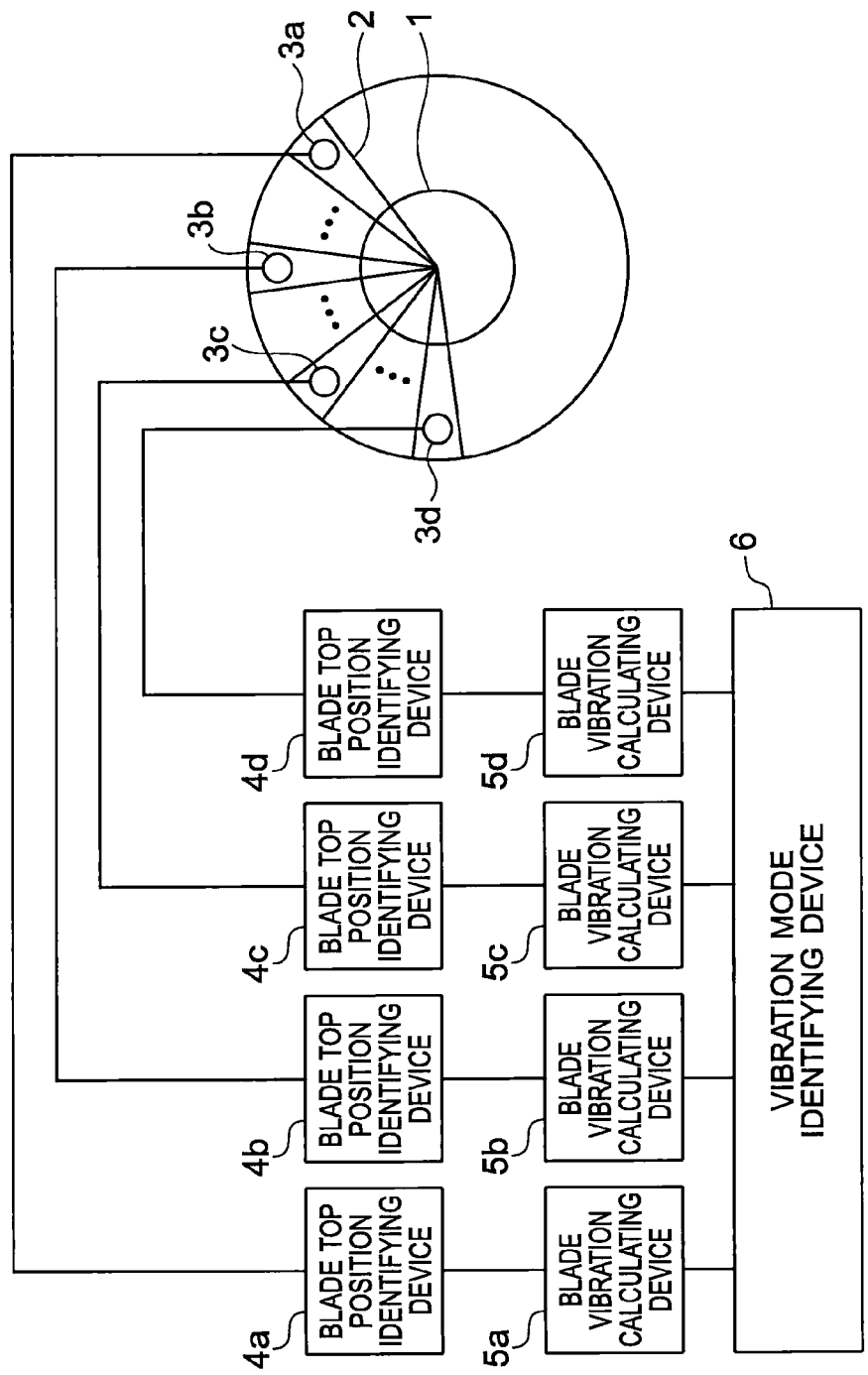
FIG. 4 is an explanatory view illustrating arrangement and a block structure of a blade vibration measuring apparatus according to a second embodiment.

FIG. 4 illustrates a structure of a blade vibration measuring apparatus according to a second embodiment of the present invention. Here, the same numeral is given to the same structural component as the abovementioned first embodiment and description thereof will not be repeated.

In the abovementioned first embodiment, the contactless displacement sensor 3 is solely used. The second embodiment is different therefrom in a point that a plurality of contactless displacement sensors 3 is arranged along a circumferential direction of the turbine moving blade 2.

Here, as illustrated in FIG. 4, four contactless displacement sensors 3a, 3b, 3c, 3d are arranged along the circumferential direction of the turbine moving blade 2. In accordance with the arrangement of the four contactless displacement sensors 3a, 3b, 3c, 3d, four blade top position identifying devices 4a, 4b, 4c, 4d and four blade vibration calculating devices 5a, 5b, 5c, 5d are arranged respectively in a separated manner. Further, there is provided a vibration mode identifying device 6 which identifies a 30 vibration mode number as receiving blade vibration signals indicating the vibration amplitude and the vibration frequency of the turbine moving blade 2 output from the blade vibration calculating devices 5a, 5b 5c, 5d.

The contactless displacement sensors 3a, 3b, 3c, 3d 35 respectively measure distance against the rotating turbine moving blade 2 and the obtained displacement measurement signals are respectively input to the corresponding blade top position identifying devices 4a, 4b, 4c, 4d. The blade top position identifying devices 4a, 4b, 4c, 4d respectively output blade top position identification signals indicating the blade top positions respectively identified based on the voltage waveform of the displacement measurement signal to the corresponding blade vibration calculating devices 5a, 5b, 5c, 5d.

The blade vibration calculating devices 5a, 5b, 5c, 5d calculate the vibration amplitude and the vibration frequency of the turbine moving blade 2 based on the obtained blade top position identification signals indicating the respective blade top positions and the obtained result is output to the vibration mode identifying device 6.

The vibration mode identifying device 6 identifies the vibration mode number of the turbine moving blade 2 based on the vibration amplitude and the vibration frequency detected at the circumferential positions of the turbine moving blade 2 where the contactless displacement sensors 3a, 3b, 3c, 3d are arranged.

According to the second embodiment as being similar to the first embodiment, time and cost required for the measurement can be reduced by directly measuring the displacement of the turbine moving blade in the rotation axis direction with the contactless displacement sensors. In addition, the vibration mode number can be identified by using the plurality of contactless displacement sensors.

The contactless displacement sensors are required to be twice as many as the vibration mode number which is required to be observed. For example, four pieces of the contactless displacement sensors are required to observe a second-order mode. 30 Here, increase of the number of the contactless displacement sensors causes cost increase owing to necessity to arrange the blade top position identifying devices and the blade vibration calculating devices respectively in the same number as the above. Accordingly, it is necessary to evaluate such cost when setting the 35 vibration mode number which is required to be observed.

(Third Embodiment)

Figure 5B:
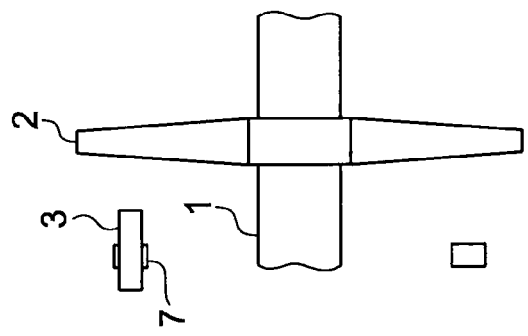
FIGS. 5A and 5B are a front view and side view illustrating arrangement and a block structure of a blade vibration measuring apparatus according to a third embodiment.
Figure 5A:
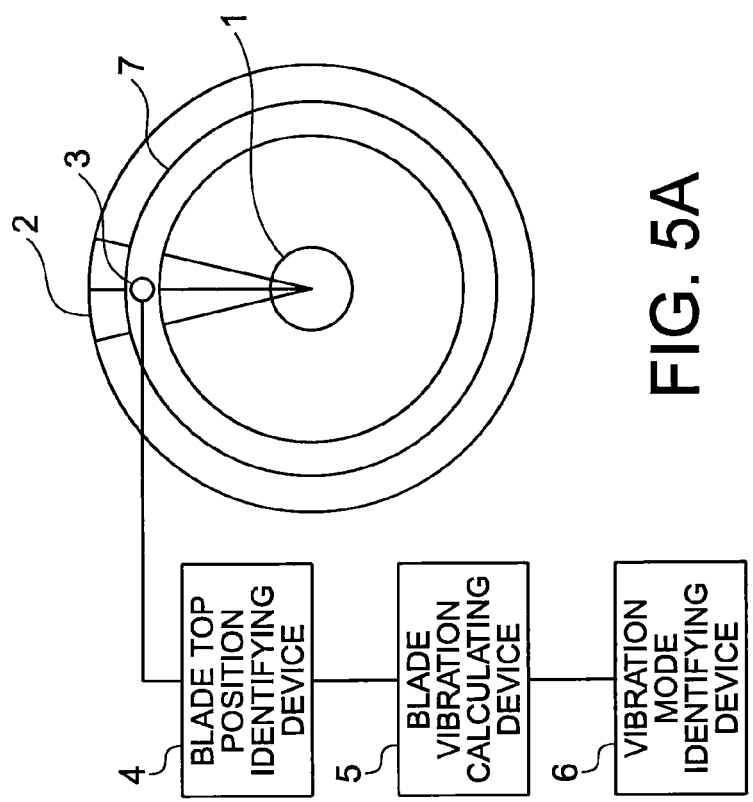

A third embodiment of the present invention will be described by using FIG. 5A being a front view and a block diagram and FIG. 5B being a side view indicating a structure thereof.

In the first embodiment and the second embodiment described above, the contactless displacement sensor 3 is attached as being in parallel to the rotary shaft 1 of the turbine moving blade 2. In contrast, a third embodiment is characteristic in that a single contactless displacement sensor 3 is arranged at a rotary jig 7 which is perpendicular to the rotary shaft 1 and which is capable of being driven to rotate coaxially with the rotary shaft 1. Here, the same numeral is given to the same structural component as the abovementioned first and second embodiments and description thereof will not be repeated.

Owing to that the contactless displacement sensor 3 is moved as the rotary jig 7 being rotationally driven, vibration of the turbine moving blade 2 can be measured by the contactless displacement sensor 3 at different positions of the turbine moving blade 2 having the same radius. Specifically, the measurement is performed as moving the contactless displacement sensor 3 to a desired position by using the rotary jig 7 while the turbine moving blade 2 is rotating. With the above, the single contactless displacement sensor 3 can provide operations and effects which are similar to those in the case of measuring vibration at a plurality of positions of the turbine moving blade 2 by using a plurality of contactless displacement sensors 3.

Similarly to the abovementioned first embodiment, the displacement measurement signal output from the contactless displacement sensor 3 is provided to the blade top position identifying device 4 and the top position of the turbine moving blade 2 is identified. Then, the result thereof is provided to the blade vibration calculating device 5 as the blade top position identification signal and the vibration amplitude and the vibration frequency of the turbine moving blade 2 are calculated. Further, similarly to the abovementioned second embodiment, the blade top position identifying device 4 identifies the top position of the turbine moving blade 2 with the displacement measurement signal output from the contactless displacement sensor 3 which is moved to different positions of the turbine moving blade 2 having the same radius. Then, the blade vibration calculating device 5 calculates the vibration amplitude and the vibration frequency, and as being based thereon, the vibration mode identifying device 6 identifies the vibration mode number of the turbine moving blade 2.

According to the third embodiment as being similar to the abovementioned first embodiment, time and cost required for the measurement can be reduced by directly measuring the displacement of the turbine moving blade in the rotation axis direction with the contactless displacement sensor. In addition, since the vibration mode number can be identified with the single contactless displacement sensor as being similar to the case of using the plurality of contactless displacement sensors, cost reduction can be achieved.

(Fourth Embodiment)

Figure 6B:
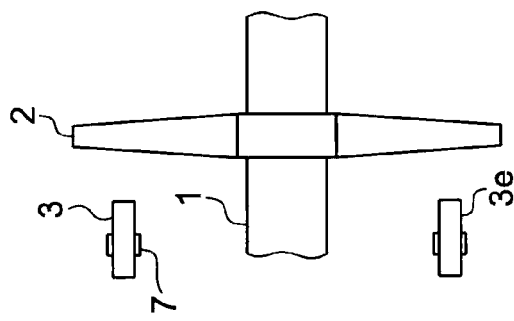
FIGS. 6A and 6B are a front view and side view illustrating arrangement and a block structure of a blade vibration measuring apparatus according to a fourth embodiment.
Figure 6A:
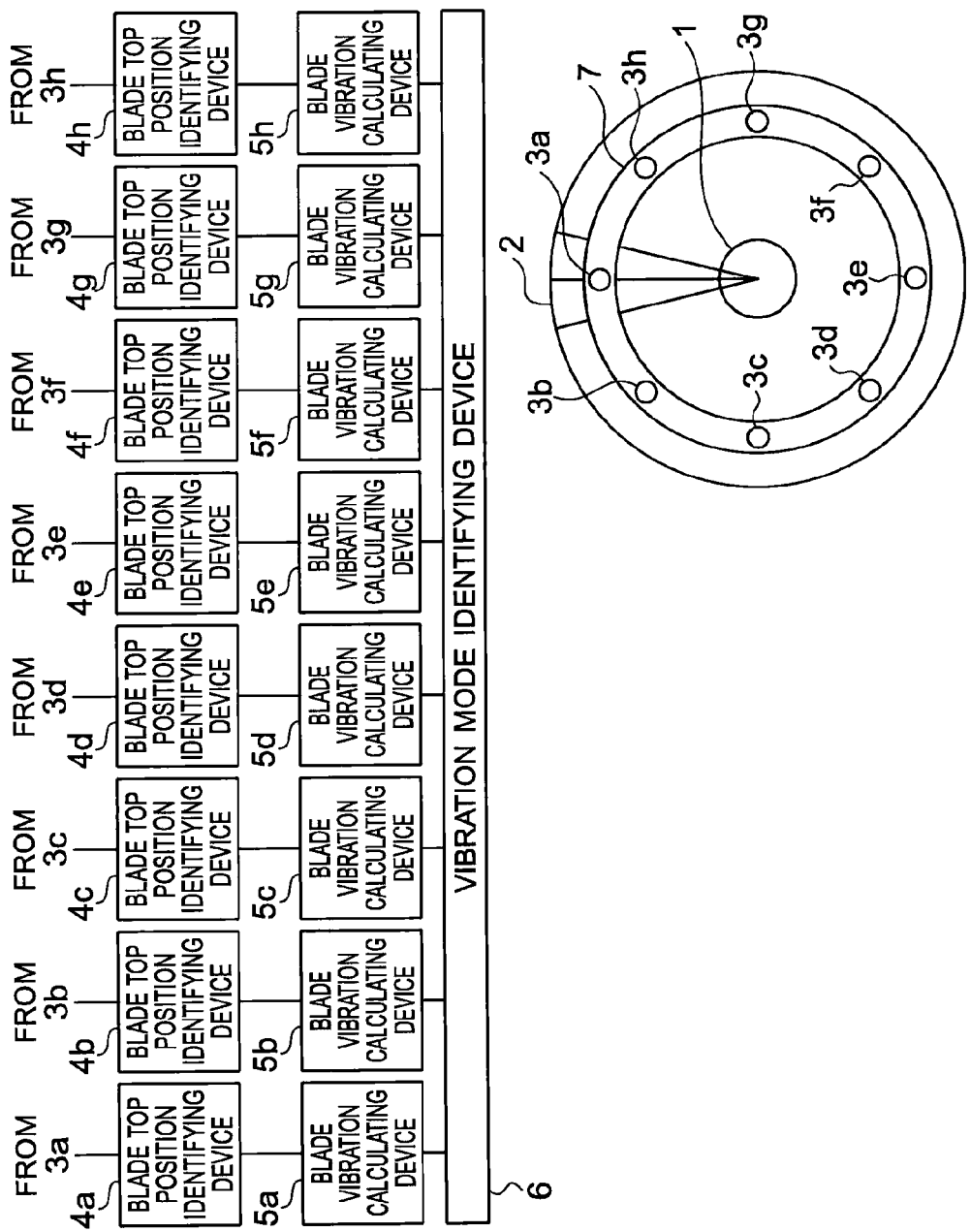

A fourth embodiment of the present invention will be described by using FIG. 6 indicating a structure thereof.

In the abovementioned third embodiment, the single contactless displacement sensor 3 is arranged at the rotary jig 7 which is perpendicular to the rotary shaft 1 and which is capable of being driven to rotate coaxially with the rotary shaft 1. In contrast, the fourth embodiment is characteristic in that a plurality of contactless displacement sensors 3a, 3b, 3c, 3d, 3e, 3f, 3g, 3h are arranged at the rotary jig 7 capable of being driven to rotate arranged as being perpendicular to the rotary shaft 1 and being coaxial with the rotary shaft 1. According to the above, eight blade top position identifying devices 4a, 4b, 4c, 4d, 4e, 4f, 4g, 4h and eight blade vibration calculating devices 5a, 5b, 5c, 5d, 5e, 5f, 5g, 5h are arranged respectively corresponding to the eight contactless displacement sensors 3a, 3b, 3c, 3d, 3e, 3f, 3g, 3h. In addition, the vibration mode identifying device 6 is arranged. Here, the same numeral is given to the same structural component as the abovementioned first to third embodiments and description thereof will not be repeated.

Displacement measurement signals at respective positions are output from the eight contactless displacement sensors 3a to 3h and blade top positions are identified by the corresponding blade top position identifying devices 4a to 4h. The result thereof is provided to the blade vibration calculating devices 5a to 5h and the vibration frequency and the vibration amplitude of the turbine moving blade 2 are calculated, and then, the vibration mode number is identified by the vibration mode identifying device 6.

According to the fourth embodiment as being similar to the abovementioned first embodiment, time and cost required for the measurement can be reduced by directly measuring the displacement of the turbine moving blade in the rotation axis direction with the contactless displacement sensors. In addition, owing to that vibration of the turbine moving blade 2 is measured by the contactless displacement sensors 3a to 3h at different positions having the same radius with the rotary jig 7 being driven to rotate, similar effects to the case of increasing the number of the contactless displacement sensors 3 can be obtained while reducing cost by reducing the number of the contactless displacement sensors 3.

In the fourth embodiment, the eight contactless displacement sensors 3a to 3h are arranged, and further, the respective positions thereof can be moved by the rotary jig 7. Accordingly, the vibration mode number being a fourth-order mode or higher can be detected.

(Fifth Embodiment)

Figure 7:
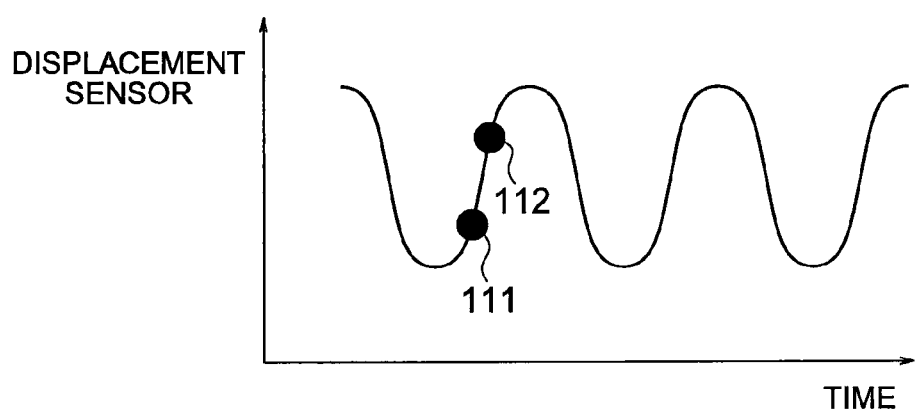
FIG. 7 is a graph illustrating a displacement curve which indicates a displacement in a rotation axis direction obtained by a blade vibration measuring apparatus according to a fifth embodiment.

A fifth embodiment of the present invention will be described by using FIG. 7 indicating a structure thereof.

The fifth embodiment is structured to include at least two of the contactless displacement sensors 3 which are arranged as being adjacent along the circumferential direction of the turbine moving blade 2 in the structure of the abovementioned fourth embodiment. The rest of the structure is the same as the abovementioned fourth embodiment and description thereof will not be repeated.

Owing to that at least two of the contactless displacement sensors 3 are adjacent, measurement signals of displacements at two adjacent measurement points are output respectively to the subsequent corresponding blade top position identifying devices. At a displacement curve indicating the displacement in the rotation axis direction indicated by the displacement measurement signal, the two adjacent positions indicated by dots 111, 112 are specified as illustrated in FIG. 7. Accordingly, it is possible to identify a displacement curve corresponding to the vibration mode number of the turbine moving blade 2.

That is, owing to that at least two of the contactless displacement sensors 3 are arranged at an interval on the turbine moving blade 2 corresponding to a half cycle of the displacement curve which corresponds to a vibration mode number to be measured, it is possible to identify the displacement curve corresponding to the vibration mode number of the turbine moving blade 2.

According to the fifth embodiment as being similar to the abovementioned first embodiment, time and cost required for the measurement can be reduced by directly measuring the displacement of the turbine moving blade in the rotation axis direction with the contactless displacement sensors. In addition, the displacement curve corresponding to the vibration mode number can be identified by adjacently arranging at least two of the contactless displacement sensors.

(Sixth Embodiment)

A sixth embodiment of the present invention will be described by using FIG. 8 indicating a structure thereof.

A sixth embodiment is characteristic in that a revolution speed adjusting device 8 is arranged at the rotary shaft 1 and that a resonant frequency detecting device 12 which detects a resonant frequency based on the vibration amplitude and the vibration frequency output from the blade vibration calculating device 5 is arranged in addition to the structure of the abovementioned first embodiment. The rest of the structure is the same as the abovementioned first embodiment and description will not be repeated as providing the same numeral to the same structural component.

Owing to that the resonant frequency detecting device 12 detects vibration amplitude of the turbine moving blade 2 at the time when the vibration amplitude measured accordingly and calculated by the blade vibration calculating device 5 becomes maximal as revolution speed of the rotary shaft 1 being varied by the revolution speed adjusting device 8 little by little, it is possible to obtain the resonant frequency at the time when a resonant phenomenon occurs at the turbine moving blade 2.

According to the sixth embodiment as being similar to the abovementioned first embodiment, time and cost required for the measurement can be reduced by directly measuring the displacement of the turbine moving blade in the rotation axis direction with the contactless displacement sensor. In addition, the resonant frequency can be obtained by arranging the revolution speed adjusting device at the rotary shaft.

(Seventh Embodiment)

A seventh embodiment of the present invention will be described by using FIG. 7.

Figure 8:
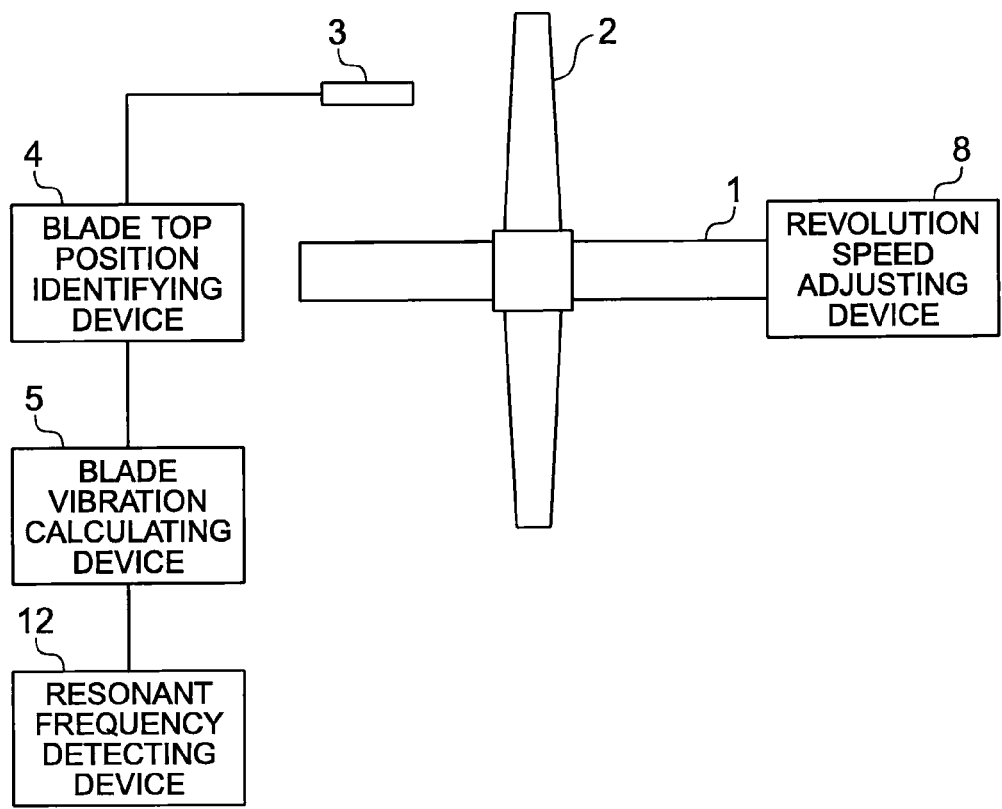
FIG. 8 is an explanatory view illustrating arrangement and a block structure of a blade vibration measuring apparatus according to a sixth embodiment.

The seventh embodiment has the similar structure to the abovementioned sixth embodiment illustrated in FIG. 8 and redundant description will not be repeated.

In the structure illustrated in FIG. 8, first, vibration amplitude measured and calculated at the time when the turbine moving blade 2 is rotated at predetermined revolution speed is memorized at the resonant frequency detecting device 12 as reference vibration amplitude.

Figure 9:
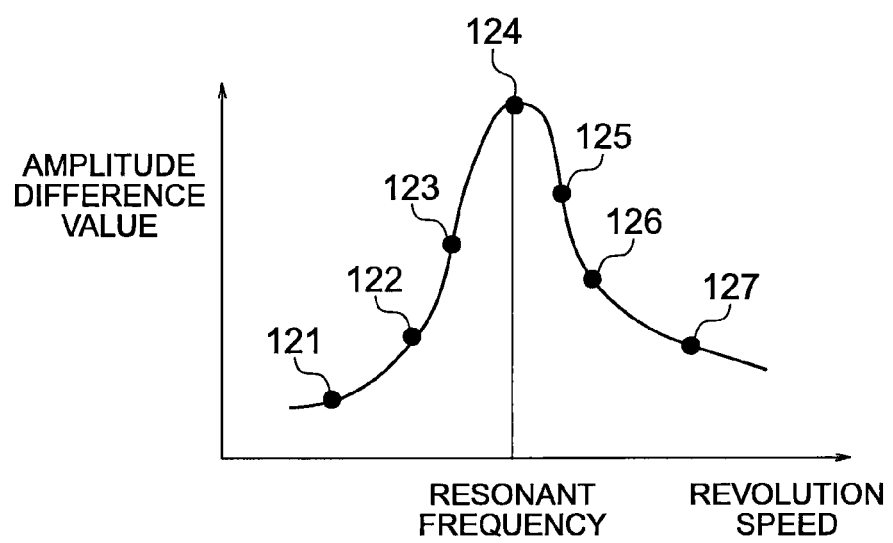
FIG. 9 is a graph indicating a method to obtain a resonant frequency from output obtained by a blade vibration measuring apparatus according to a seventh embodiment.

Next, the revolution speed of the rotary shaft 1 is varied by the revolution speed adjusting device 8 and the resonant frequency detecting device 12 calculates an amplitude difference value between the reference vibration amplitude and the vibration amplitude measured and calculated at that time. Each time when the revolution speed is varied, the amplitude difference value between the reference vibration amplitude and the vibration amplitude at that time is to be calculated with the abovementioned procedure. FIG. 9 indicates a graph in which the amplitude difference values against the revolution speed obtained as described above are plotted with dots 121, 122, 123, . . . .

The resonant frequency of the turbine moving blade 2 can be calculated by the resonant frequency detecting device 12 based on a maximal value indicated by the dot 124 in the graph or a minimal value (not illustrated).

Here, owing to performing the process to obtain the abovementioned amplitude difference value for each turbine blade 2, measurement errors caused by an attaching error and a geometric error of each turbine blade 2 are cancelled.

Further, the process to obtain the abovementioned amplitude difference value is sequentially performed each time when the revolution speed of the rotary shaft 1 is varied. Accordingly, measurement errors caused by influences such as thermal expansion of the turbine moving blade 2 occurring when the revolution speed is varied, expansion due to centrifugal force, and leaning of the turbine moving blade 2 due to rotation are cancelled as well.

According to the seventh embodiment as being similar to the above mentioned first embodiment, time and cost required for the measurement can be reduced by directly measuring the displacement of the turbine moving blade in the rotation axis direction with the contactless displacement sensor. In addition, the resonant frequency can be obtained by obtaining amplitude difference values as varying the revolution speed of the rotary shaft 1.

(Eighth Embodiment)

Figure 10:
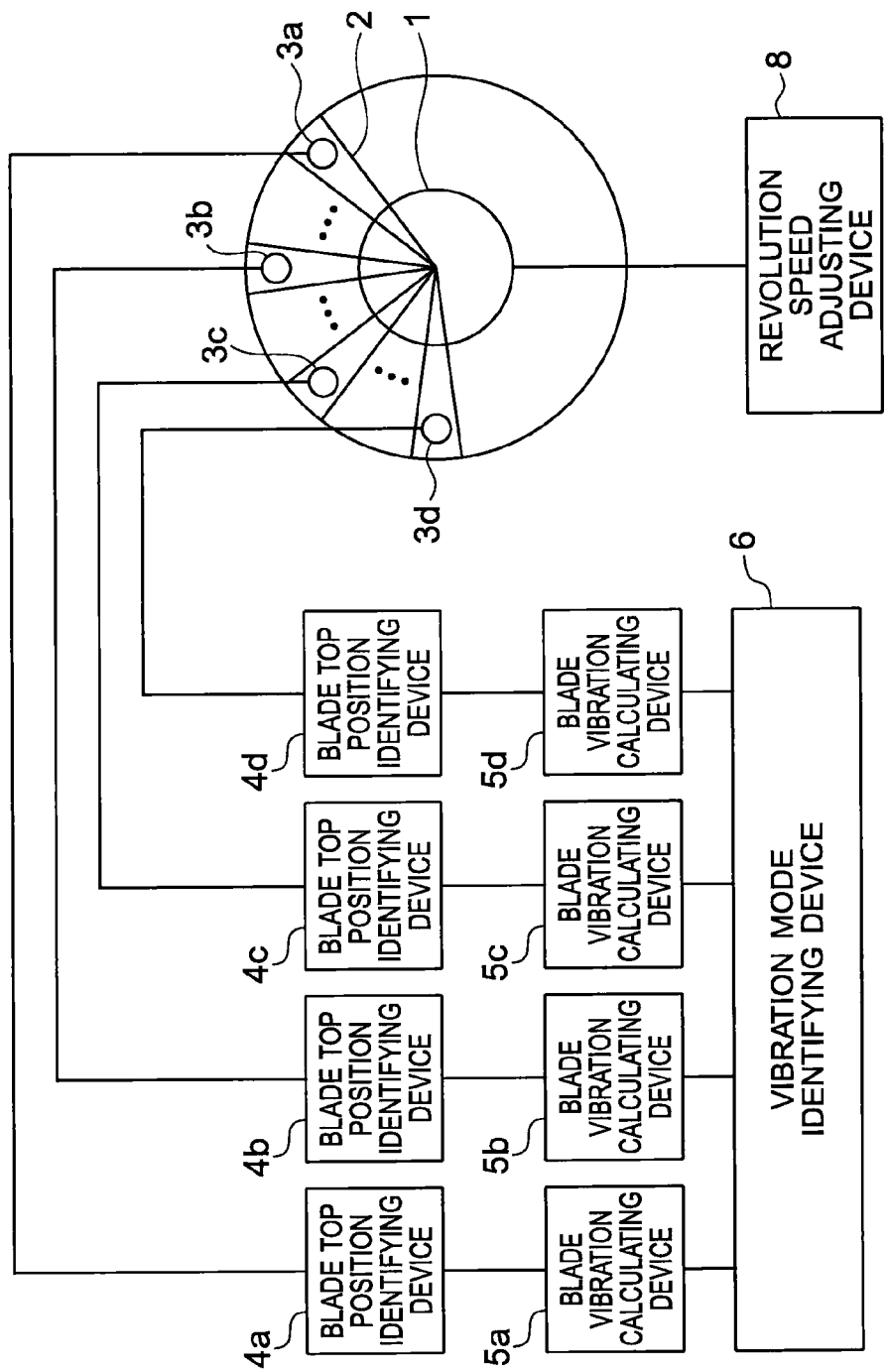
FIG. 10 is an explanatory view illustrating arrangement and a block structure of a blade vibration measuring apparatus according to an eighth embodiment.

An eighth embodiment of the present invention will be described by using FIG. 10 indicating a structure thereof.

In an eighth embodiment, the revolution speed adjusting device 8 is further arranged at the rotary shaft 1 in addition to the structure of the second embodiment illustrated in FIG. 4.

Figure 11:
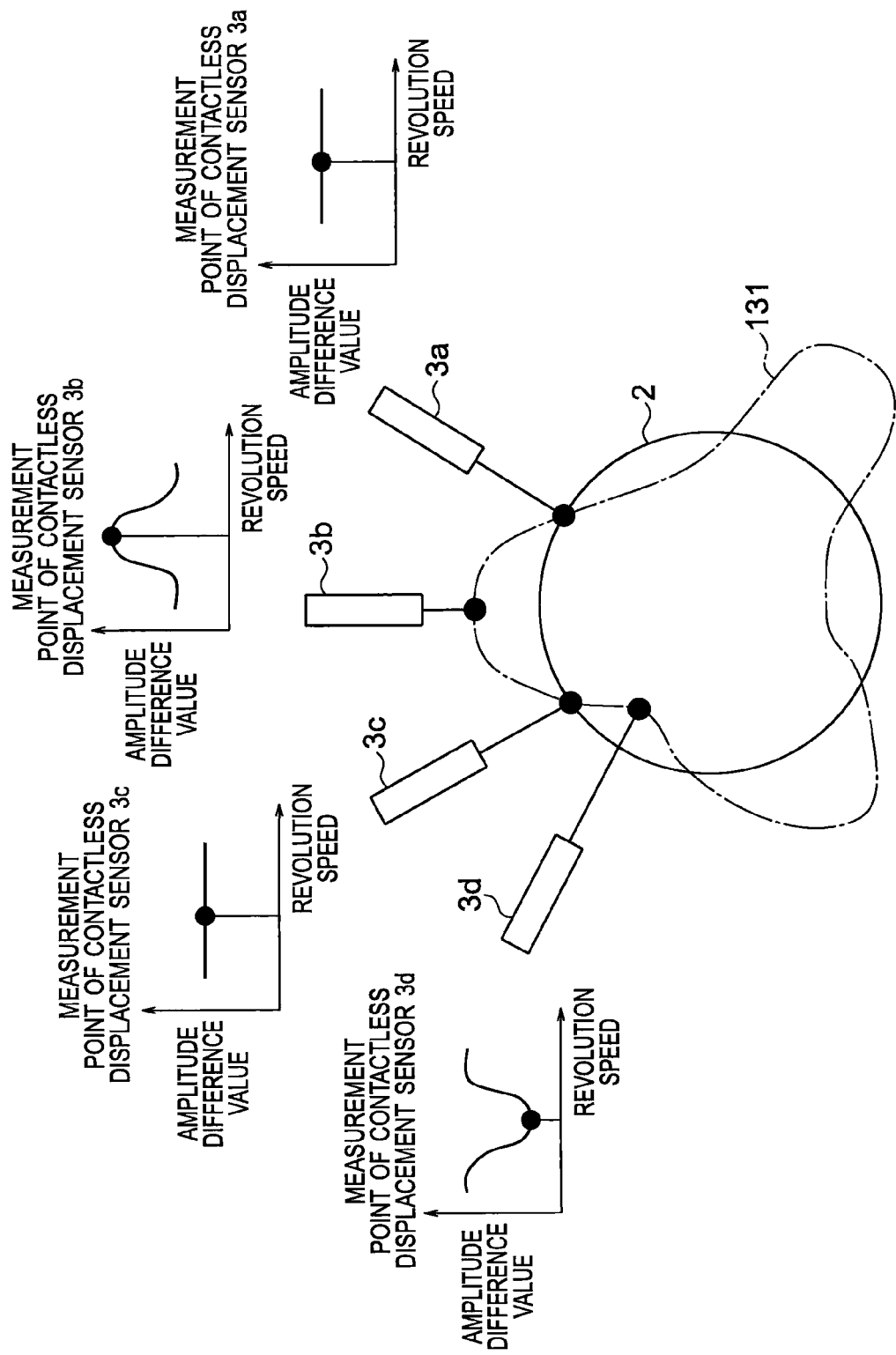
FIG. 11 is an explanatory view and graphs indicating a method to obtain a vibration mode number from output obtained by the blade vibration measuring apparatus according to the eighth embodiment.

FIG. 11 illustrates a state that a resonant phenomenon occurs at the turbine moving blade 2 while the revolution speed of the rotary shaft 1 is varied by the revolution speed adjusting device 8. Here, FIG. 11 schematically illustrates a state of capturing displacements of the turbine moving blade 2 in the rotation axis direction in a third-order resonant mode illustrated by a dash-dotted line 131 using four contactless displacement sensors 3a to 3d. At positions where the contactless displacement sensors 3a and 3c are arranged, the amplitude is almost zero as corresponding to nodes. At a position where the contactless displacement sensor 3b is arranged, the amplitude becomes a maximal value as corresponding to an antinode. At a position where the contactless displacement sensor 3d is arranged, the amplitude becomes a minimal value.

According to the eighth embodiment as being similar to the abovementioned first embodiment, time and cost required for the measurement can be reduced by directly measuring the displacement of the turbine moving blade in the rotation axis direction with the contactless displacement sensors. In addition, it is possible to identify the resonant mode by arranging the plurality of contactless displacement sensors in the circumferential direction of the turbine moving blade 2 at appropriate intervals and further obtaining the vibration amplitude at the time when the resonant phenomenon is generated by the revolution speed adjusting device 8.

(Ninth Embodiment)

A ninth embodiment of the present invention will be described by using FIGS. 12 and 13 indicating a structure thereof.

Figure 12:
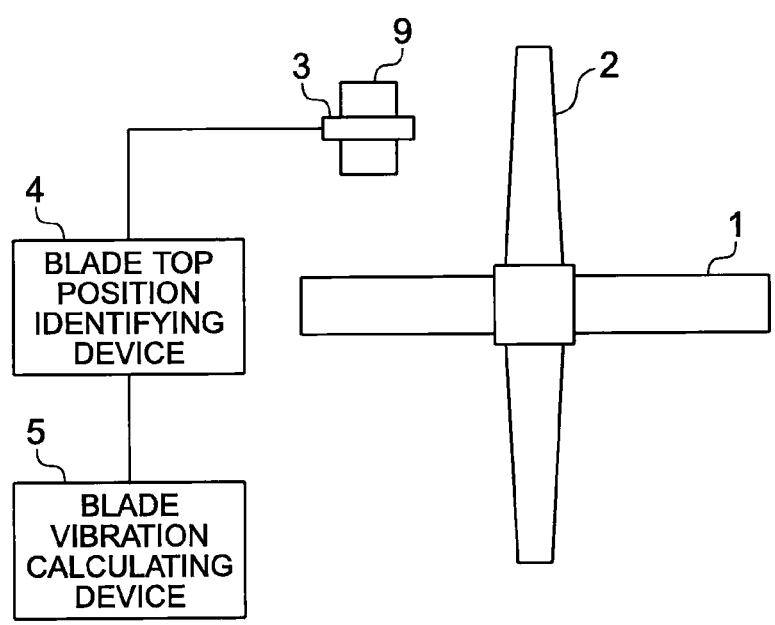
FIG. 12 is an explanatory view illustrating arrangement and a block structure of a blade vibration measuring apparatus according to a ninth embodiment.

As illustrated in FIG. 12, a ninth embodiment further includes an angle adjusting device 9 which adjusts an angle of the contactless displacement sensor 3 in addition to the structure of the abovementioned first embodiment illustrated in FIG. 1. The same numeral is given to the same structural component as the abovementioned first embodiment and description thereof will not be repeated.

In general, a contactless displacement sensor is used for measuring a distance against a parallel flat plate and output voltage thereof becomes the maximum when a relative angle against a target plane is normal.

Figure 13A:
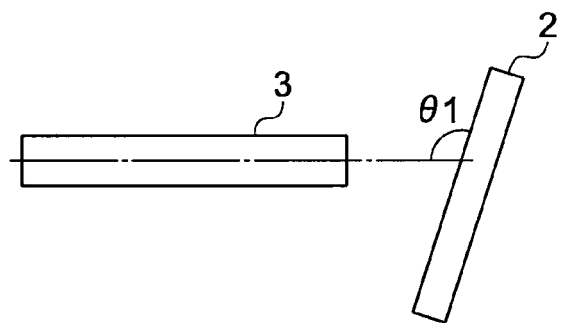
FIGS. 13A to 13C are explanatory views indicating a method enabling to obtain an output value having desired magnitude as adjusting a relative angle of a contactless displacement sensor against a turbine moving blade by using an angle adjusting device in the blade vibration measuring apparatus according to the ninth embodiment.
Figure 13B:
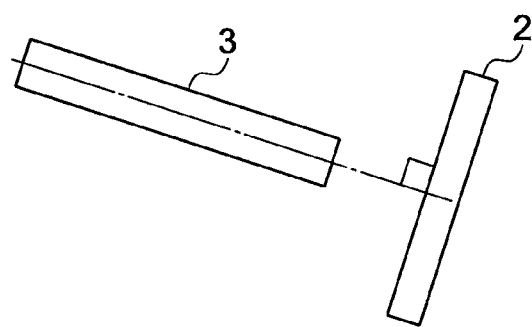
Figure 13C:
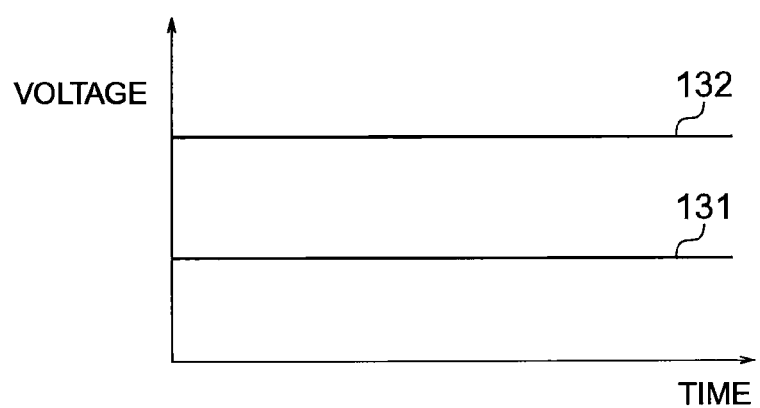

Output voltage obtained when the contactless displacement sensor 3 has an angle θ1 being different from 90° against a plane of the turbine moving blade 2 as illustrated in FIG. 13A is indicated 10 by line 131 in FIG. 13C. Further, output voltage obtained when the contactless displacement sensor 3 has 90° against the plane of the turbine moving blade 2 as illustrated in FIG. 13B is indicated by line 132 in FIG. 13C. To obtain the maximum output voltage as line 132, the contactless displacement sensor 3 is required to be set at 90° against the plane of the turbine moving blade 2.

For example, in a case that the contactless displacement sensor 3 is arranged as being in parallel to the rotary shaft 1, the contactless displacement sensor 3 is in a state of not being arranged at 90° against the plane of the turbine moving blade 2 when the plane of the turbine moving blade 2 is inclined against the rotary shaft 1 approximately by 10°.

Accordingly, the relative angle against the turbine moving blade 2 is set to be 90° by previously adjusting the angle of the contactless displacement sensor 3 by using the angle adjusting device 9 before starting the measurement.

According to the ninth embodiment as being similar to the abovementioned first embodiment, time and cost required for the measurement can be reduced by directly measuring the displacement of the turbine moving blade in the rotation axis direction with the contactless displacement sensor. In addition, output of the contactless displacement sensor can be maximized.

Here, in the ninth embodiment, not only being added to the structure of the abovementioned first embodiment, the angle adjusting device 9 may be added to the structures of the abovementioned second to eighth embodiments.

(Tenth Embodiment)

Figure 14:
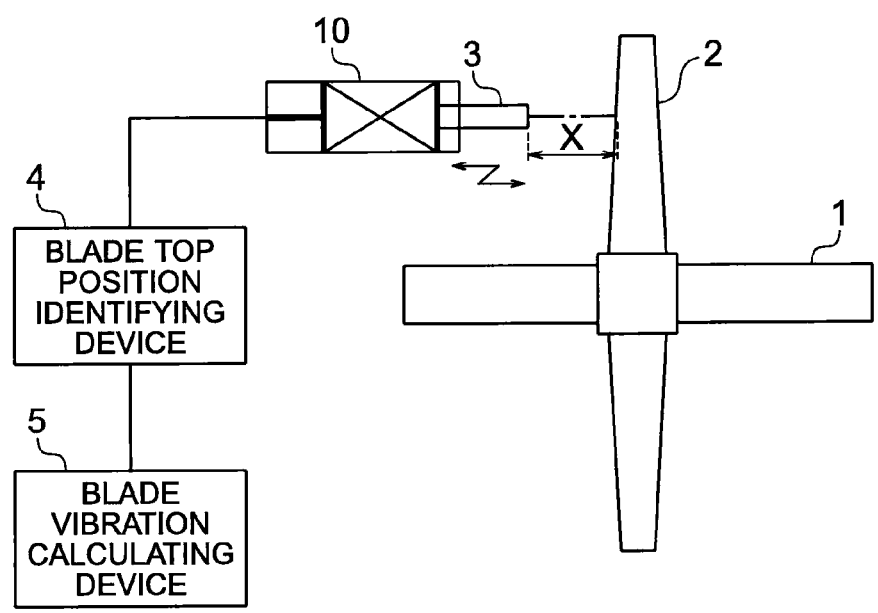
FIG. 14 is an explanatory view illustrating arrangement and a block structure of a blade vibration measuring apparatus according to a tenth embodiment.

A tenth embodiment of the present invention will be described by using FIG. 14 indicating a structure thereof.

A tenth embodiment is characteristic in that a distance adjusting device 10 is attached to the contactless displacement sensor 3 in addition to the structure of the abovementioned first embodiment. Here, the same numeral is given to the same structural component and description thereof will not be repeated. In general, with a contactless displacement sensor, output magnitude is proportional to a distance against an object and the measurable distance is previously determined. Accordingly, as illustrated by an arrow in FIG. 14, the distance X is adjusted by moving the contactless displacement sensor 3 in the rotation axis direction of the turbine moving blade 2 before starting the measurement, so that desired magnitude of output can be obtained.

According to the tenth embodiment as being similar to the abovementioned first embodiment, time and cost required for the measurement can be reduced by directly measuring the displacement of the turbine moving blade in the rotation axis direction with the contactless displacement sensor. In addition, it is possible to adjust the distance between the turbine moving blade 2 and the contactless displacement sensor 3 so that desired magnitude of output can be obtained from the contactless displacement sensor 3.

Here, in the tenth embodiment, not only being added to the structure of the abovementioned first embodiment, the distance adjusting device 10 may be added to the structures of the abovementioned second to ninth embodiments.

(Eleventh Embodiment)

Figure 15:
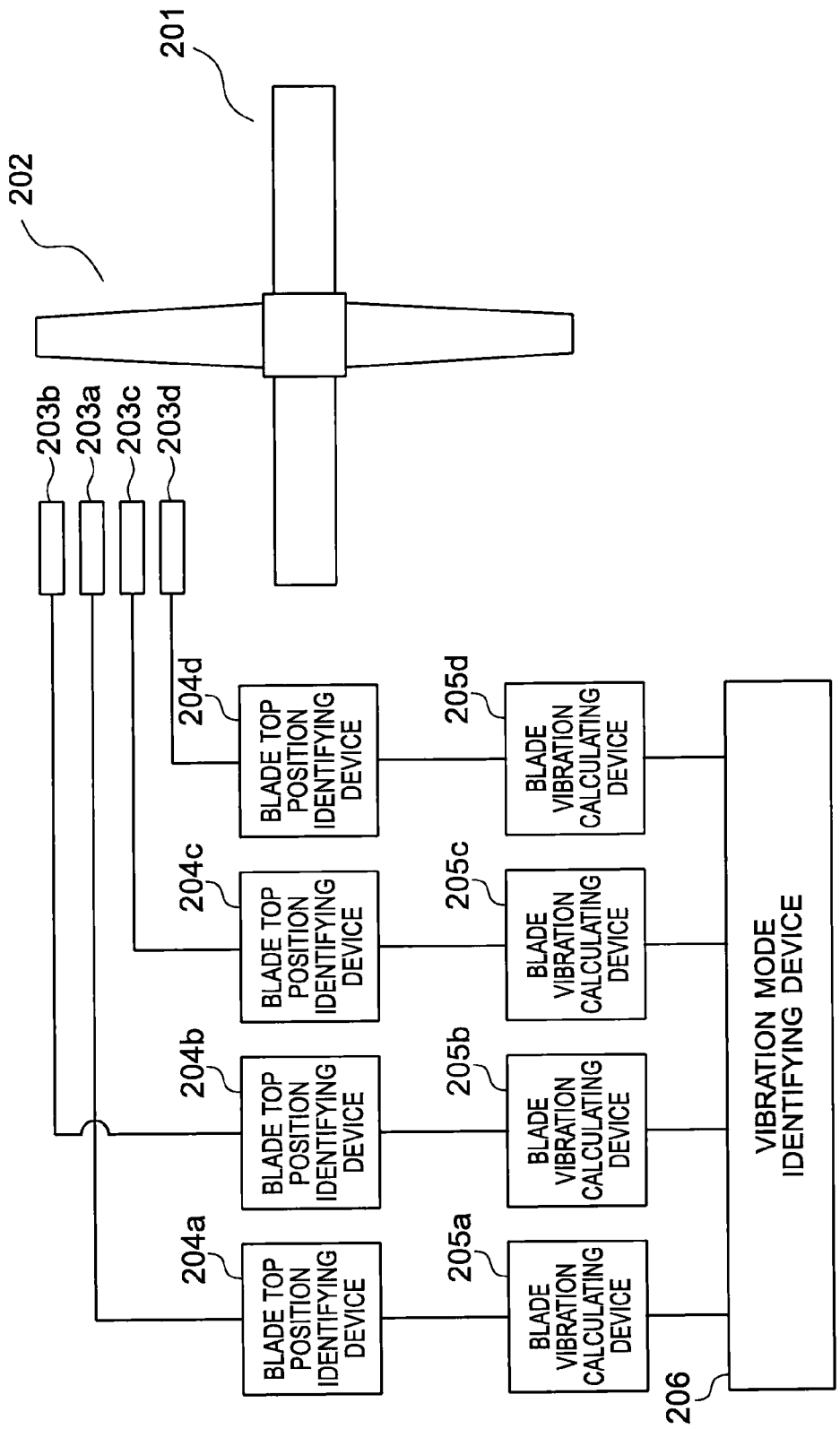
FIG. 15 is a block diagram and front view illustrating a structure of a blade vibration measuring apparatus according to an eleventh embodiment.
Figure 16:
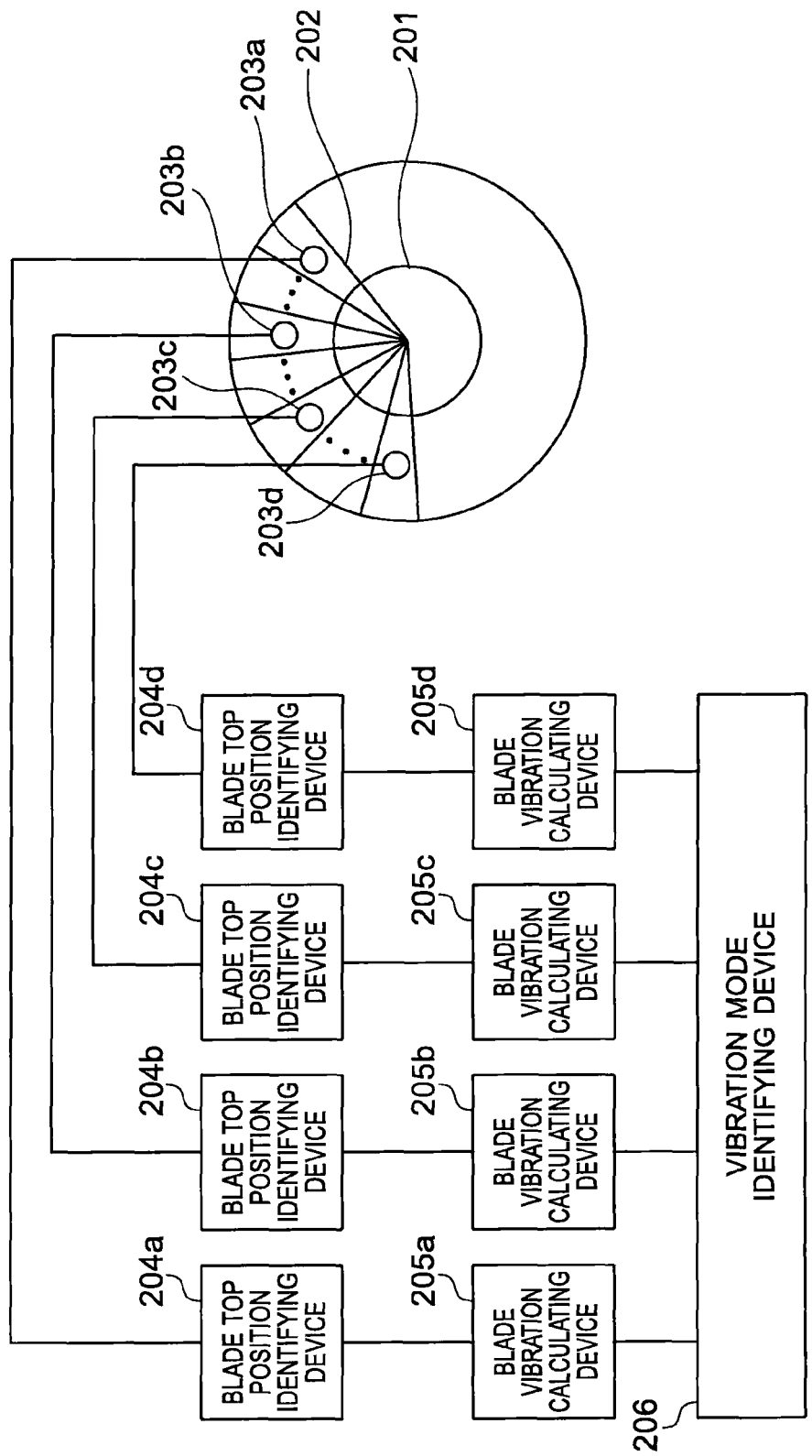
FIG. 16 is a block diagram and side view illustrating a structure of a blade vibration measuring apparatus according to the eleventh embodiment.

FIG. 15 is a front view and FIG. 16 is a side view of a turbine moving blade 202 as illustrating a structure of an eleventh embodiment of the present invention.

To measure displacements in a rotation axis direction of the turbine moving blade 202 attached to a rotary shaft 201, a plurality of contactless displacement sensors 203a, 203b, 203c, 203d is arranged on the same radius at predetermined intervals in a circumferential direction of the turbine moving blade 202.

Displacement measurement signals output from the respective contactless displacement sensors 203a, 203b, 203c, 203d are input to corresponding blade top position identifying devices 204a, 204b, 204c, 204d. Then, identification of the top positions of the turbine blade 202 is performed and blade top position identification signals indicating the result thereof are output.

The top position identification signals are provided to corresponding blade vibration calculating devices 205a, 205b, 205c, 205d and vibration amplitude and a vibration frequency of the turbine moving blade 202 are calculated and output to a vibration mode identifying device 206.

A vibration mode number is obtained at the vibration mode identifying device 206 based on the vibration amplitude and vibration frequency at each arranging position of the contactless displacement sensors 203a, 203b, 203c, 203d.

Here, a method to identify blade top positions at the blade top position identifying devices 204a, 204b, 204c, 204d will be described by using FIGS. 17A and 17B.

Figure 17A:
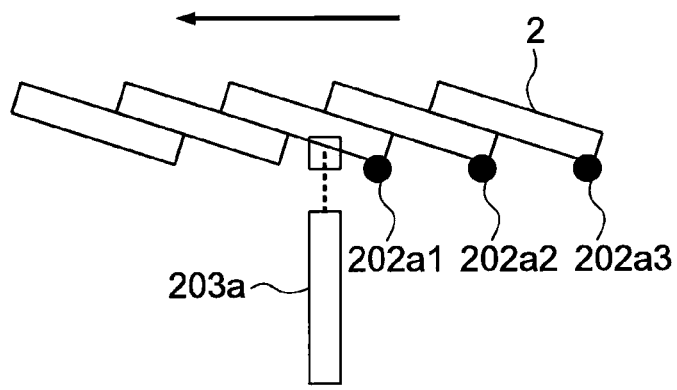
FIGS. 17A and 17B are explanatory views indicating a method to identify a blade top position according to the eleventh embodiment.

As illustrated in FIG. 17A, a blade row of the turbine moving blade 202 is rotated and moved in a direction indicated by an arrow. Owing to that the blade row of the turbine moving blade 202 passes through the front of the contactless displacement sensor 203a as an example among the contactless displacement sensors 203a, 203b, 203c, 203d, a displacement measurement signal having a voltage waveform as illustrated in FIG. 17B is output from the contactless displacement sensor 203a. Here, a detection position of the turbine moving blade 202 by the contactless displacement sensor 203a indicated by a square in FIG. 17A corresponds to a position indicated by a square on the output voltage waveform in FIG. 17B.

Figure 17B:
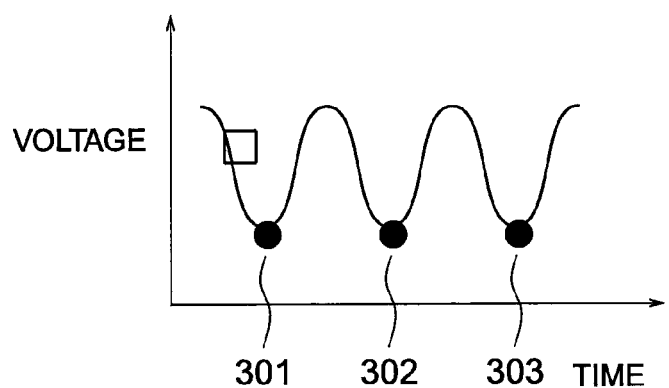

Further, top positions of the turbine moving blade 202 indicated by dots 202a1, 202a2, 202a3 in FIG. 17A correspond to lowermost peak values of the output voltage waveform indicated by dots 301, 302, 303 in FIG. 17B.

A method of calculating the vibration amplitude and the vibration frequency of the turbine blade 202 with the blade vibration calculating device 205 will be described by using FIGS. 18A and 18B.

Figure 18A:
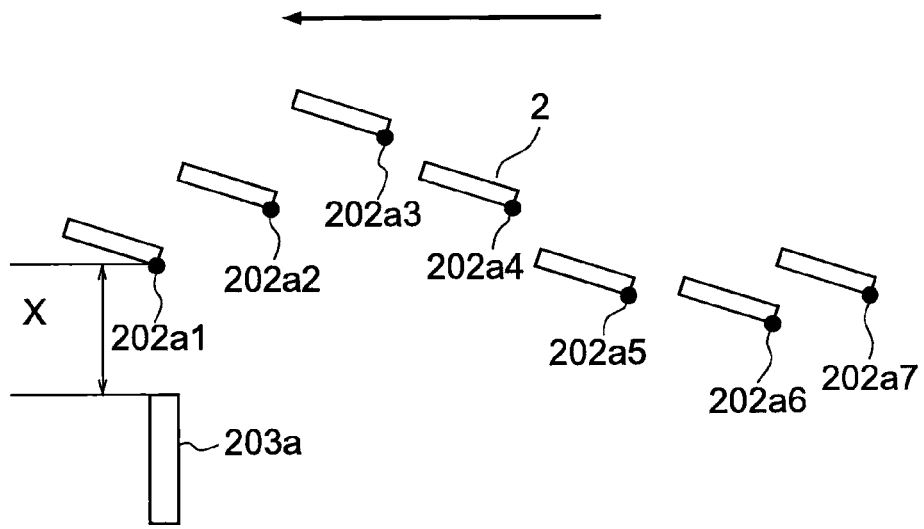
FIGS. 18A and 18B are explanatory views indicating a method to calculate blade vibration amplitude and a vibration frequency according to the eleventh embodiment.
Figure 18B:
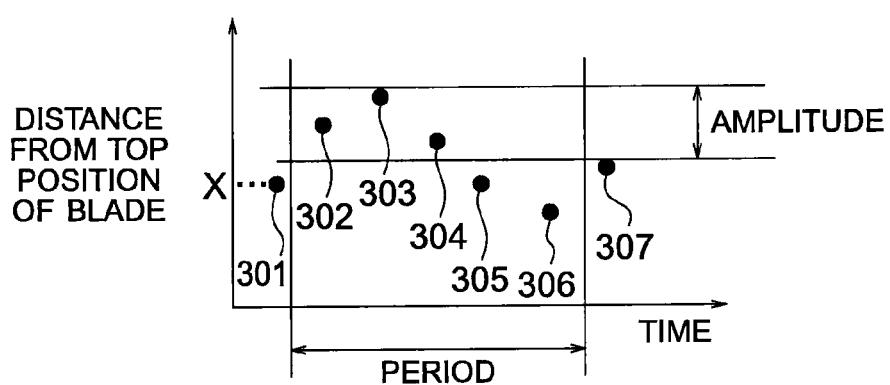

As illustrated in FIG. 18A, when vibration occurs at the turbine moving blade 202, the distance X from the top positions of the turbine moving blade 202 indicated by dots 202a1, 202a2, 10 202a3, 202a4, 202a5, 202a6, 202a7 to the contactless displacement sensor 203a is fluctuated. This fluctuation becomes the fluctuation of the lowermost peak value of the output voltage waveform indicated by the dots 301, 302, 303, 304, 305, 306, 307 described by using FIG. 17B. Accordingly, the voltage corresponding to the blade top position output from the blade top position identifying device 204a is converted into a relative distance between the blade top position and the contactless displacement sensor 203a at the blade vibration calculating device 205a and the obtained relative distance is recorded in chronological order as illustrated in FIG. 18B. The vibration amplitude and the vibration frequency of the turbine moving blade 202 can be calculated from the chronological data recorded as described above.

Further, the eleventh embodiment is characteristic in that curve fitting is performed at the time of identifying top positions of the turbine moving blade 202 respectively at the blade top position identifying devices 204a, 204b, 204c, 204d.

In FIG. 19A, the distance to the turbine moving blade 202 is measured by the contactless displacement sensor 203a, for example, among the contactless displacement sensors 203a, 203b, 203c, 203d, 203e, 203f. Distances to discontinuous blade measurement positions 202a11, 202a12, 202a13, 202a14, 202a115 corresponding to sampling timing at the turbine moving blade 202 are measured when the turbine moving blade 202 passes through the front of the contactless displacement sensor 203a and displacement measurement signals are output.

When the displacement measurement signals are input to the blade top position identifying device 204a, measurement values at the discontinuous blade measurement positions 202a11, 202a12, 202a13, 202a14, 202a15 are sampled and memorized.

Then, owing to that curb fitting is performed, for example, by using a least square method or the like to interpolate between the respective blade measurement positions 202a11, 202a12, 202a13, 202a14, 202a15 with measurement values thereat, a curve S as illustrated by a broken line is obtained. A blade top estimated position 202a14 is obtained from the peak value of the curve S.

When revolution speed of the turbine moving blade 202 becomes high, it becomes difficult to perform blade top position identification by using a contactless displacement sensor. Accordingly, voltage values of displacement measurement signals are obtained as being sampled from the contactless displacement sensor at a plurality of measurement positions in the vicinity of the blade top and curve fitting is performed on these values. It is possible to improve accuracy of the blade top position identification by identifying the peak value of the curve S obtained as described above as the blade top position. Although the accuracy of the blade top position identification is improved with increase of the sampling frequency, the sampling frequency may be set at the order of several hundred kHz, for example, as considering processing time and cost with increase of processing quantity.

According to the eleventh embodiment, time and cost required for the measurement can be reduced by directly measuring the displacement of the blade in the rotation axis direction accurately at a response frequency on the order of several hundred kHz instead of measuring blade passing timing.

Here, for performing curve fitting on measurement values, data indicating a profile of turbine moving blade 202 is previously stored in a storage unit (not illustrated) or the like and the curve fitting is performed by using the data, so that the curve profile of the turbine moving blade 202 can be accurately obtained. Further, although the turbine moving blade 202 is varied in shape in accordance with an operational state, the identification of the blade top position can be performed as obtaining the curve profile more accurately by storing profile data in each operational state.

(Twelfth Embodiment)

Figure 20:
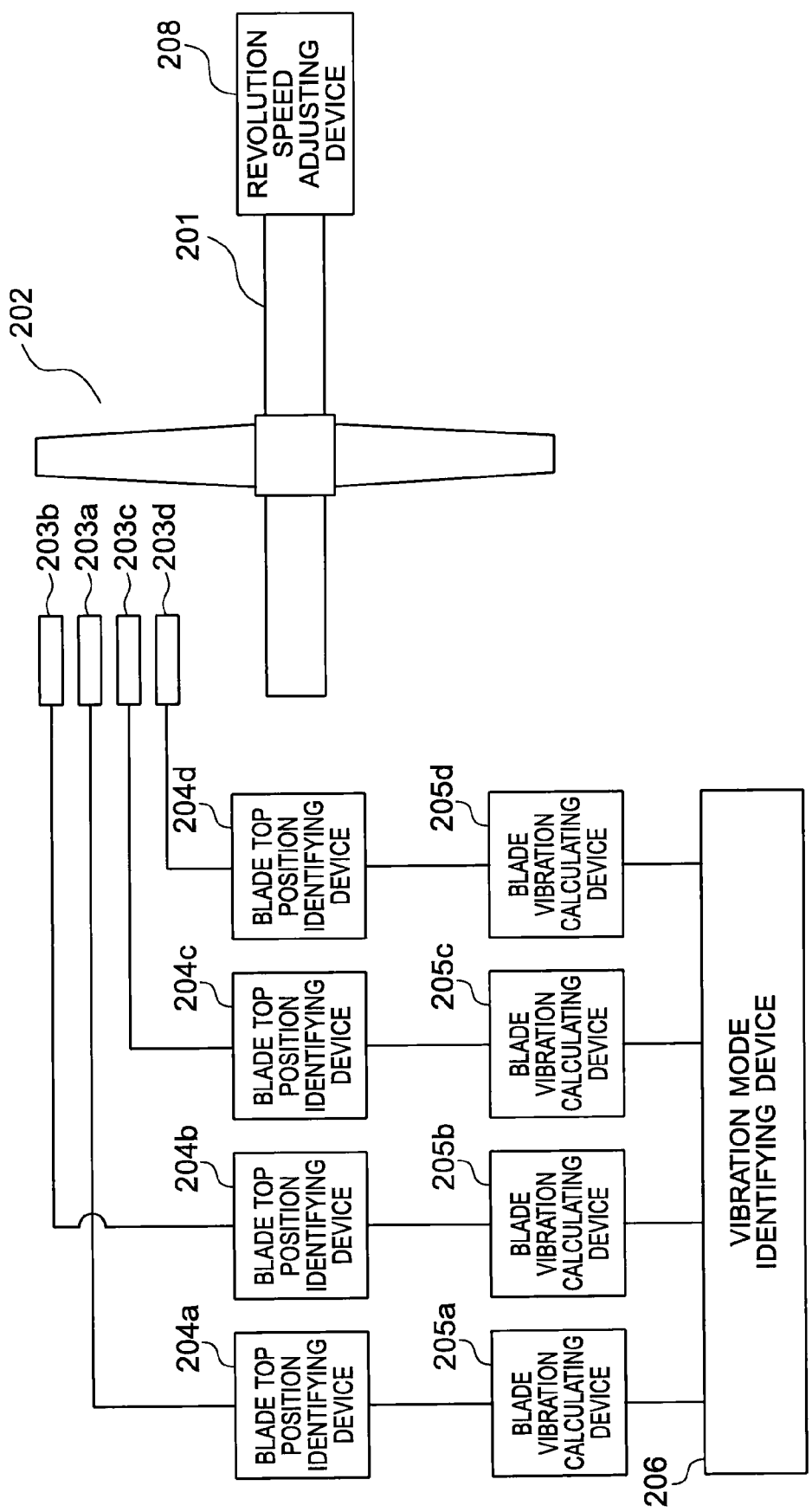
FIG. 20 is a block diagram and front view illustrating a structure of a blade vibration measuring apparatus according to a twelfth embodiment.
Figure 21:
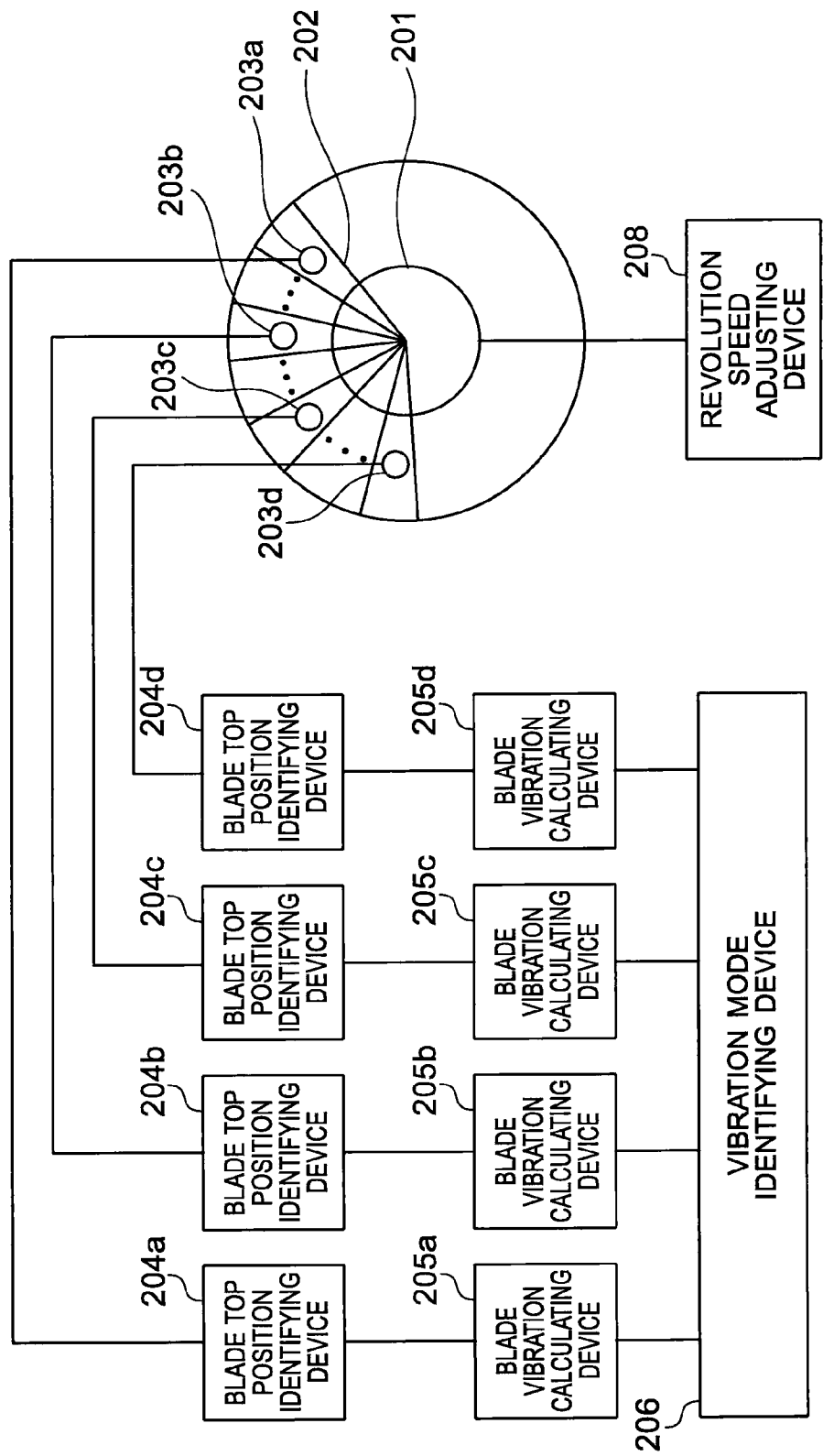
FIG. 21 is a block diagram and side view illustrating a structure of a blade vibration measuring apparatus according to the twelfth embodiment.

FIG. 20 is a front view and FIG. 21 is a side view of the turbine moving blade 202 as illustrating a structure of a twelfth embodiment of the present invention.

The twelfth embodiment is different from the abovementioned structure of the eleventh embodiment in a point that a revolution speed adjusting device 208 to vary revolution speed of the rotary shaft 201 is further arranged. The same numeral is given to the same structural component as the abovementioned eleventh embodiment and description thereof will not be repeated.

When the rotary shaft 201 is rotated at predetermined revolution speed, identification of the blade top position of the turbine moving blade 202 is performed respectively at the blade top position identifying devices 204a, 204b, 204c, 204d and the blade top position identification signals are output. Similarly to the abovementioned eleventh embodiment, the blade top position identification signals are provided to the corresponding blade vibration calculating devices 205a, 205b, 205c, 205d and the vibration amplitude and the vibration frequency of the turbine moving blade 202 are calculated and output to the vibration mode identifying device 206.

The vibration mode identifying device 206 receives the vibration amplitude and the vibration frequency from the blade vibration calculating devices 205a, 205b, 205c, 205d and receives the displacement measurement signals output from the contactless displacement sensors 203a, 203b, 203c, 203d.

At the vibration mode identifying device 206, data indicating the blade top positions included in the displacement measurement signals is sorted for each blade of the turbine moving blade 202 and determination of the resonant mode number is performed. Specifically, displacement measurement values obtained as the blades sequentially passing through the front of the respective contactless displacement sensors 203a, 203b, 203c, 203d are collected for each blade.

Figure 22:
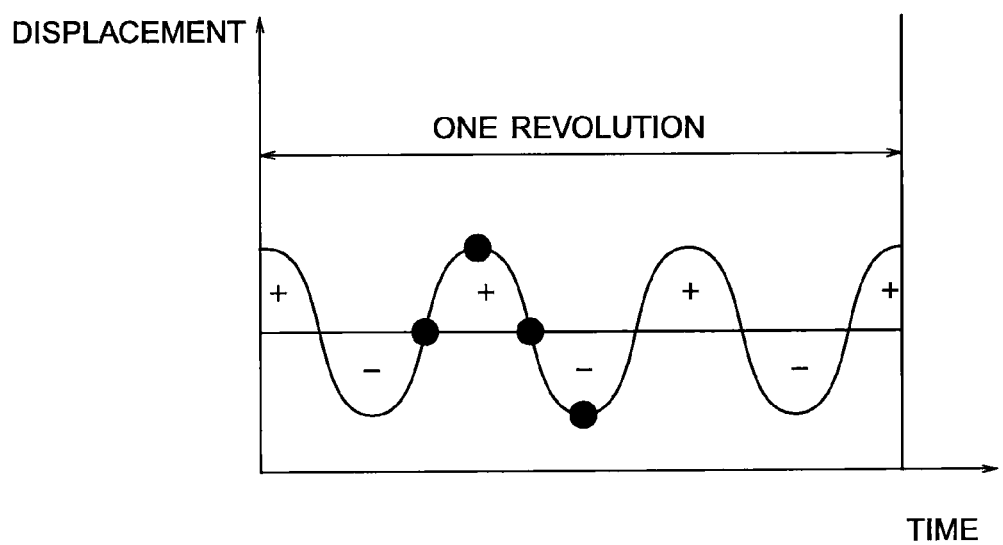
FIG. 22 is an explanatory view indicating a method to perform curve fitting as sorting blade top positions for each blade according to the twelfth embodiment.

When a resonant phenomenon occurs while the revolution 5 speed of the rotary shaft 201 is varied by the revolution speed adjusting device 208, a graph in which the displacement regularly varies while a certain blade makes one turn is obtained as illustrated in FIG. 22. A curve of the displacement variation is approximated to a sine curve. Curve fitting is performed at the vibration mode identifying device 206 on the discontinuous displacement measurement values obtained with sampling and the resonant mode is identified.

In this manner, since the number of the contactless displacement sensors 203 can be reduced by performing curve fitting on the discontinuous displacement measurement values into a sine curve in a resonant state, cost required for the measurement can be reduced.

According to the twelfth embodiment being similar to the abovementioned eleventh embodiment, time and cost required for the measurement can be reduced by directly measuring the displacement of the blade in the rotation axis direction accurately at a response frequency on the order several hundred kHz instead of measuring blade passing timing. In addition, performing curve fitting on the discontinuous displacement measurement values into a sine curve in a resonant state can contribute to cost reduction by reducing the number of the contactless displacement sensors 203.

(Thirteenth Embodiment)

Figure 23:
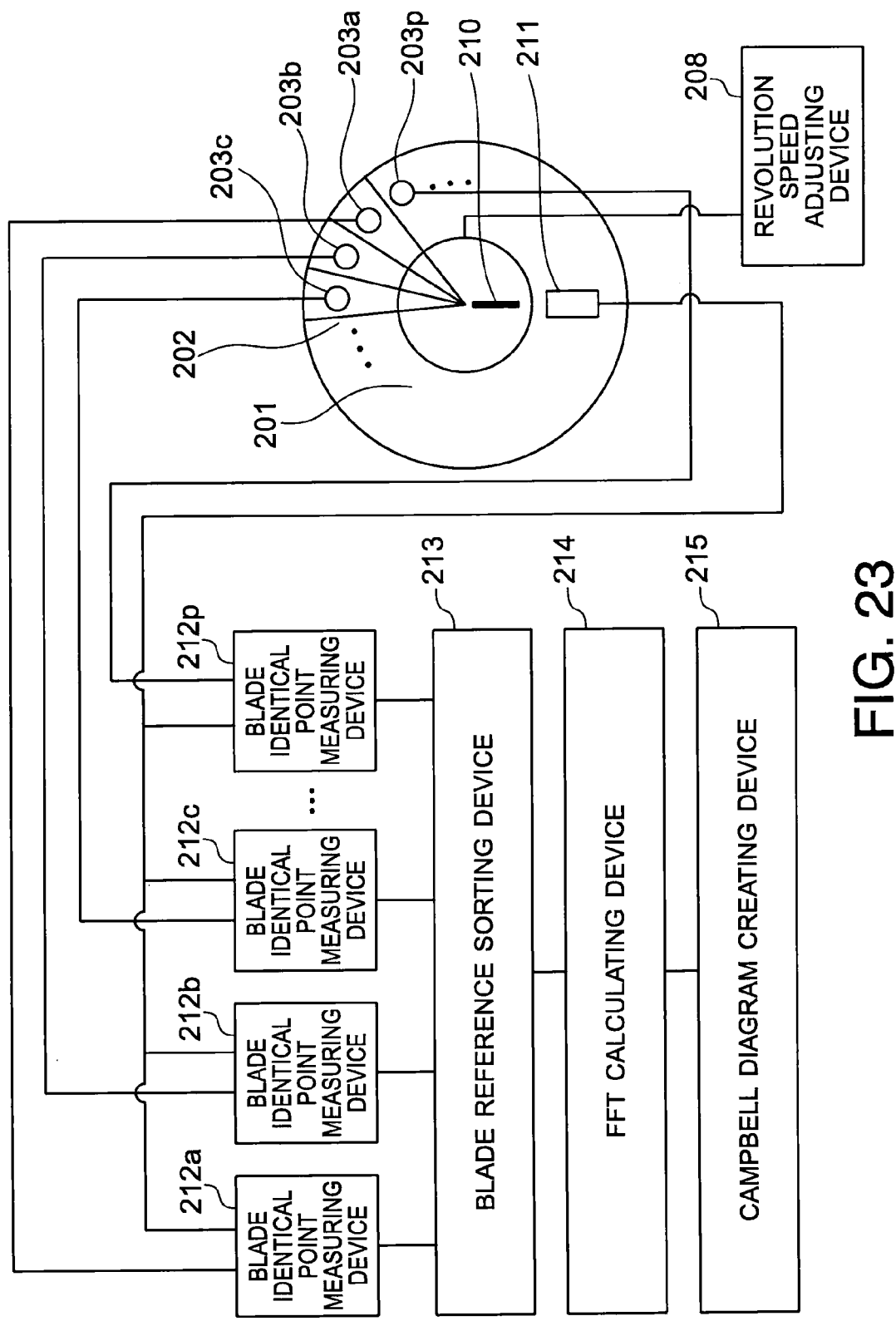
FIG. 23 is an explanatory view illustrating a structure of a blade vibration measuring apparatus according to a thirteenth embodiment.

A thirteenth embodiment of the present invention will be described by using FIG. 23.

Sixteen contactless displacement sensors 203a, 203b, 203c, ..., 203p are arranged along the circumferential direction of the turbine moving blade 202.

Further, a rotational synchronization pulse generating device 211 is arranged at a predetermined position of the turbine moving blade 202. A rotational synchronization pulse is generated each time when any blade of the turbine moving blade 202 passes through the predetermined position and is provided to the respective contactless displacement sensors 203a, 203b, 203c, ..., 203p.

According to the above, at the contactless displacement sensors 203a, 203b, 203c, ..., 203p, the displacement measurement signals indicating a distance (displacement) to the rotating turbine moving blade 202 at the time of receiving the rotational synchronization pulse are generated and output.

The output displacement measurement signals are provided respectively to the same number of blade identical point measuring devices 212a, 212b, 212c, ..., 212p which correspond to the contactless displacement sensors 203a, 203b, 203c, ..., 203p. At the blade identical point measuring devices 212a, 212b, 212c, ..., 212p, distances to identical points of the rotating turbine moving blade 202 are measured based on the displacement measurement singles and identical point displacement signals are output. In this manner, the identical point displacement signals are output respectively from the blade identical point measuring devices 212a, 212b, 212c, ..., 212p and are provided to a blade reference sorting device 213.

At the blade reference sorting device 213, the provided sixteen identical point displacement signals are sorted for each blade of the turbine moving blade 202 and are output as a chronological displacement signal to be provided to an FET calculating device 214.

The FET calculating device 214 performs fast Fourier transform on the chronological displacement signal sorted in accordance with each blade. The obtained result is provided to a Campbell diagram creating device 215 as a fast Fourier transform result signal.

Figure 26:
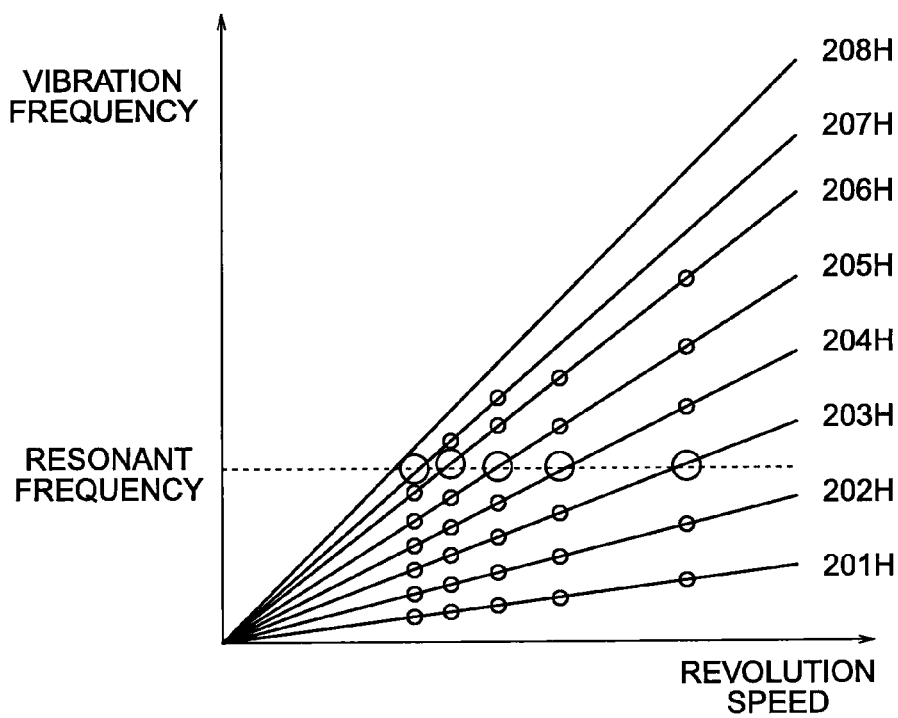
FIG. 26 is a Campbell diagram as obtaining the result of FIG. 25 for each revolution speed of the turbine moving blade and plotting with the revolution speed being the horizontal axis and the vibration frequency being the vertical axis according to the thirteenth embodiment.

The Campbell diagram creating device 215 creates a Campbell diagram described below by using FIG. 26 based on the fast Fourier transform result signal and evaluates vibration characteristics of the turbine moving blade 202. The result thereof is output to the outside as an evaluation result signal.

Figure 24A:
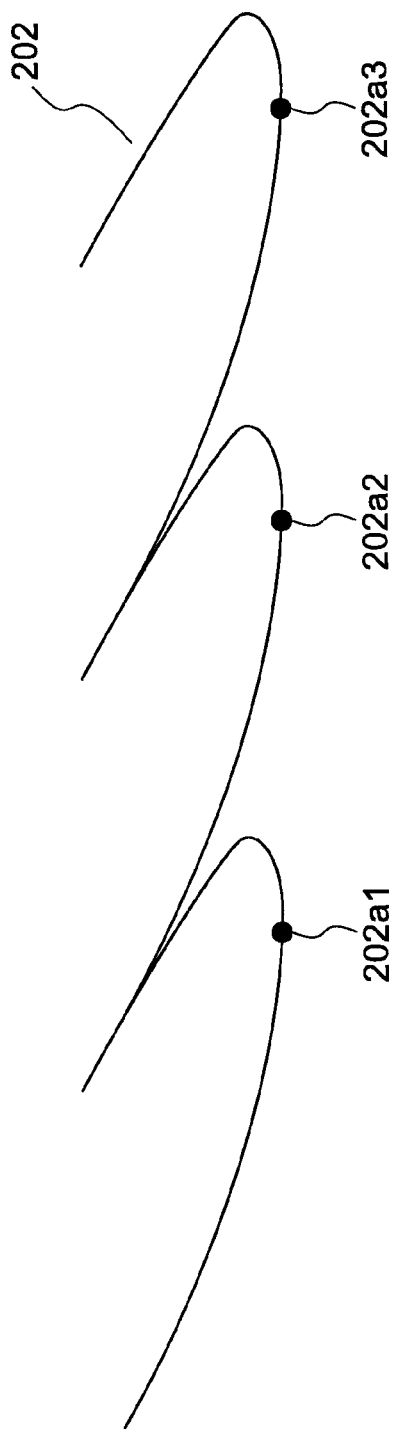
FIGS. 24A and 24B are explanatory views indicating a method to measure displacements of identical points of a turbine moving blade by using rotational synchronization pulses according to the thirteenth embodiment.
Figure 24B:
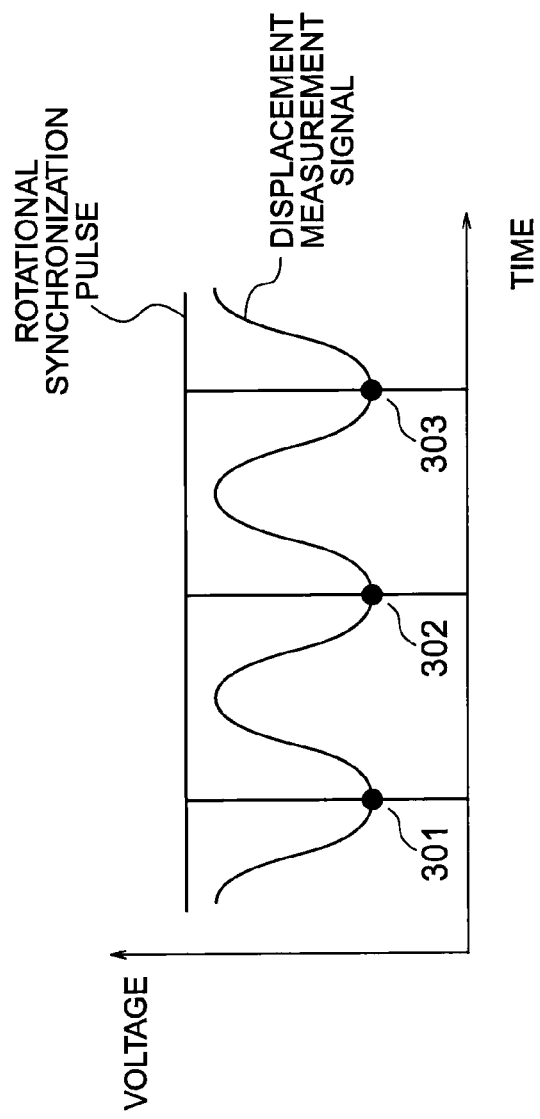

As illustrated in FIG. 24A, displacements of identical points 202a1, 202a2, 202a3 of the respective blades of the turbine moving blade 202 are required to be measured. Accordingly, displacements of the dots 301, 302, 303 corresponding to the identical points 202a1, 202a2, 202a3 of the respective blades in the displacement measurement signals output from the contactless displacement sensors 203a, 203b, 203c, ..., 203p are specified by using rotational synchronization pulses as illustrated in FIG. 24B. According to the above, displacements of the identical points of the respective blades are measured at the respective blade identical point measuring devices 212a to 212p.

Then, the measurement is performed while the revolution speed is gradually increased by the revolution speed adjusting device 208 and a resonance point and a resonant mode are to be obtained.

In general, 2×N pieces of sensors are necessary for measuring an Nth-order (N is a positive integer) resonant mode. In the thirteenth embodiment, since the sixteen contactless displacement sensors 203a to 203p are used, resonant modes can be captured up to the eighth-order.

Figure 25:
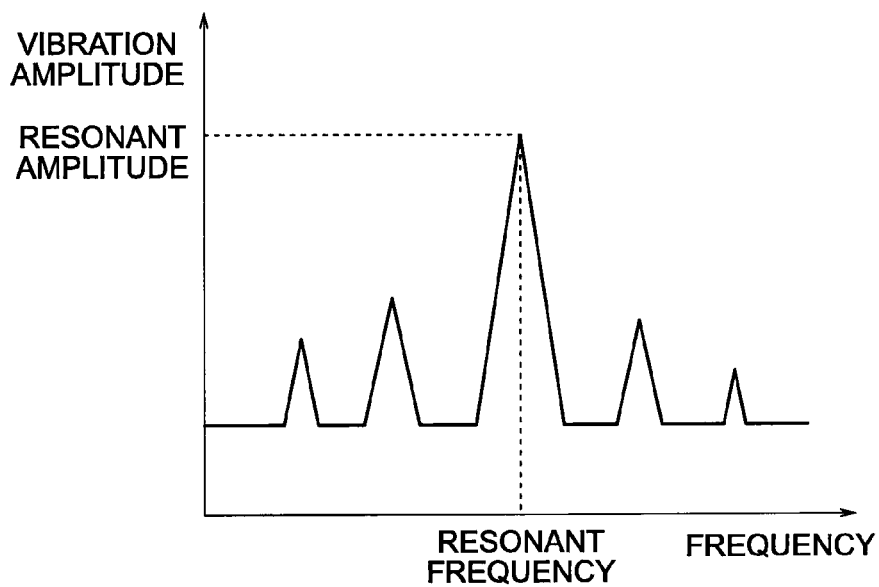
FIG. 25 is a graph indicating relation of vibration amplitude against frequencies obtained by performing fast Fourier transform on displacement signals at the identical points of the turbine moving blade according to the thirteenth embodiment.

FIG. 25 indicates relation of vibration amplitude against frequencies obtained by performing fast Fourier transform with the FET calculating device 214 on the displacement measurement signals at the identical points of the turbine moving blade 202 generated by the blade reference sorting device 213. The resonance point is denoted by timing having the maximum vibration amplitude and the frequency thereat is the resonant frequency.

Fast Fourier transform described above is to be performed for each revolution speed of the turbine moving blade 202. The obtained result is illustrated in FIG. 26 as a Campbell diagram as being plotted into a graph with the revolution speed being the horizontal axis and the vibration frequency being the vertical axis.

The Campbell diagram illustrates lines which respectively connecting predetermined-number-times of the respective rotational frequencies. For example, line 201H (H is a positive integer) denotes a line connecting one-time frequencies of the rotational frequencies, line 202H denotes a line connecting two-times frequencies of the rotational frequencies, . . . , line 208H denotes a line connecting eight-times frequencies of the rotational frequencies.

Further, sizes of white circles illustrated in the Campbell diagram are proportional to magnitude of the vibration amplitude. Accordingly, sizes of one set of while circles vertically aligned in FIG. 26 correspond respectively to the vibration amplitude from 201H to 208H at predetermined revolution speed and the one set corresponds to the vibration amplitude at the predetermined revolution speed illustrated in the graph of FIG. 25.

In the Campbell diagram created by the Campbell diagram creating device 215 as described above, the vibration frequency at which the vibration amplitude becomes large regardless of the revolution speed is estimated to be the resonant frequency at the resonance point.

According to the thirteenth embodiment being similar to the abovementioned eleventh embodiment, time and cost required for the measurement can be reduced by directly measuring the displacement of the blade in the rotation axis direction accurately at a response frequency on the order several hundred kHz instead of measuring blade passing timing. In addition, the resonant frequency can be obtained by creating a Campbell diagram.

(Fourteenth Embodiment)

A fourteenth embodiment of the present invention will be described by using FIGS. 27-30.

Figure 27:
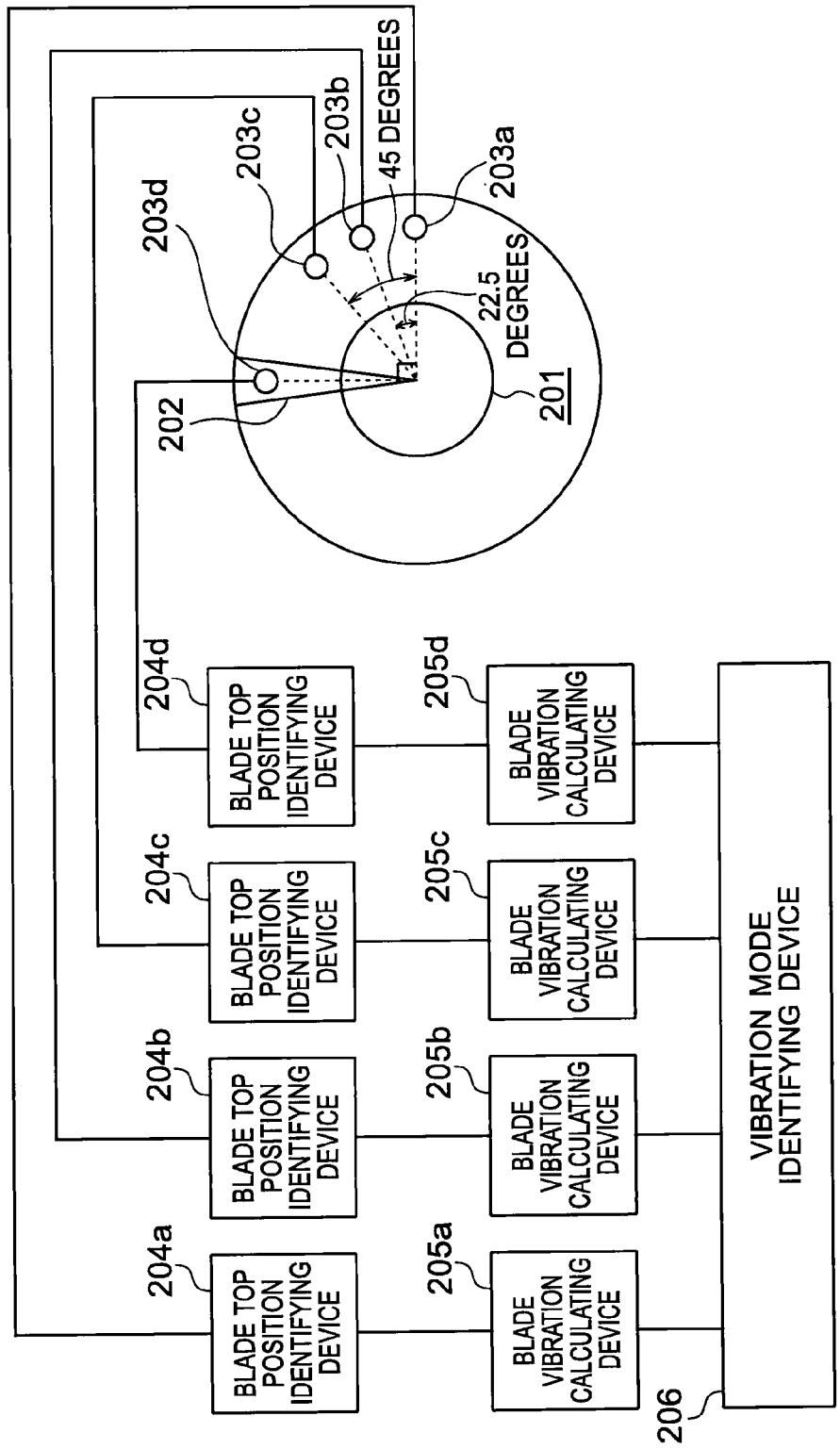
FIG. 27 is an explanatory view illustrating a structure of a blade vibration measuring apparatus according to a fourteenth embodiment.

A fourteenth embodiment has a structure illustrated in FIG. 27. Along the circumferential direction of the turbine moving blade 202, a first contactless displacement sensor 203a is arranged, a second contactless displacement sensor 203b is arranged with an angle interval being 22.5° from the first contactless displacement sensor 203a, a third contactless displacement sensor 203c is arranged with an interval being 45° from the first contactless displacement sensor 203a, and further, a fourth contactless displacement sensor 203d is arranged with an interval being 90° from the first contactless displacement sensor 203a.

The displacement measurement signals output from the contactless displacement sensors 203a, 203b, 203c, 203d are provided to the blade top position identifying devices 204a, 204b, 204c, 204d arranged respectively corresponding thereto and identification of a blade top position is performed respectively thereat. The result thereof is output respectively to the blade vibration calculating devices 205a, 205b, 205c, 205d as the blade top position identification signals.

At the blade vibration calculating devices 205a, 205b, 205c, 205d, the vibration amplitude and the vibration frequency of the turbine moving blade 202 are calculated based on the blade top position identification signals. The result thereof is provided to the vibration mode identifying device 206 as the blade vibration signal.

The vibration mode identifying device 206 identifies the vibration mode based on the vibration amplitude and the vibration frequency at positions where the contactless displacement sensors 203a to 203d are arranged.

Figure 28:
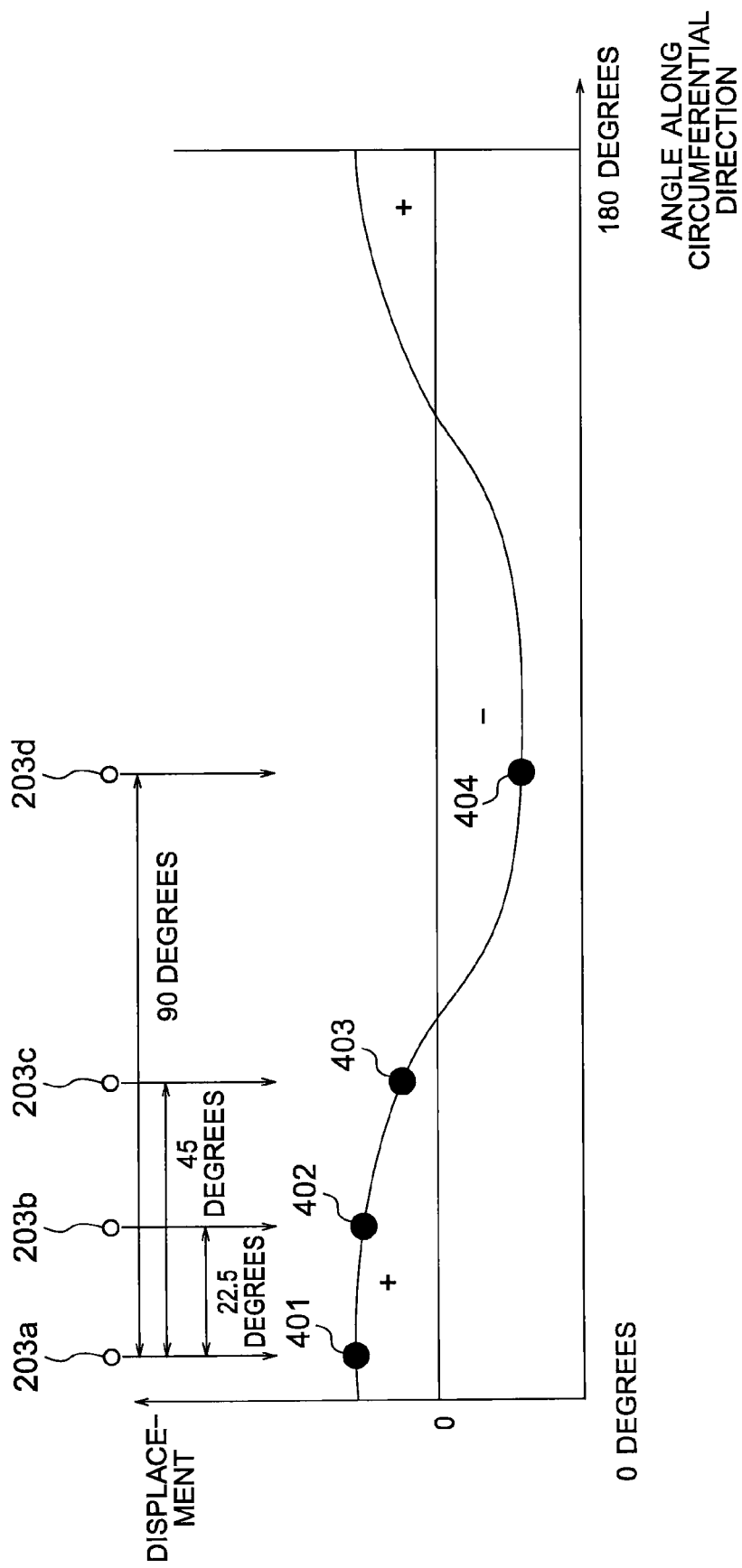
FIG. 28 is a graph indicating a displacement at the time of second-order resonant mode occurrence being capable of being measured by the blade vibration measuring apparatus according to the fourteenth embodiment.

In FIG. 28, black circles indicate displacements measured respective by the contactless displacement sensors 203a to 203d which are sequentially arranged having the abovementioned angle intervals along the circumferential direction of the turbine moving blade 202 in a case that a second-order resonant mode occurs. Similarly, displacements measured respectively by the contactless displacement sensors 203a to 203d is indicated in FIG. 29 in a case that a fourth-order resonant mode occurs and in FIG. 30 in a case that an eighth-order resonant mode occurs.

In the second-order resonant mode indicated in FIG. 28, corresponding to the arrangement positions of the contactless displacement sensors 203a to 203d, displacements of measurement points 401, 402, 403 are at the plus side and a displacement of a measurement point 404 is at the minus side.

Figure 29:
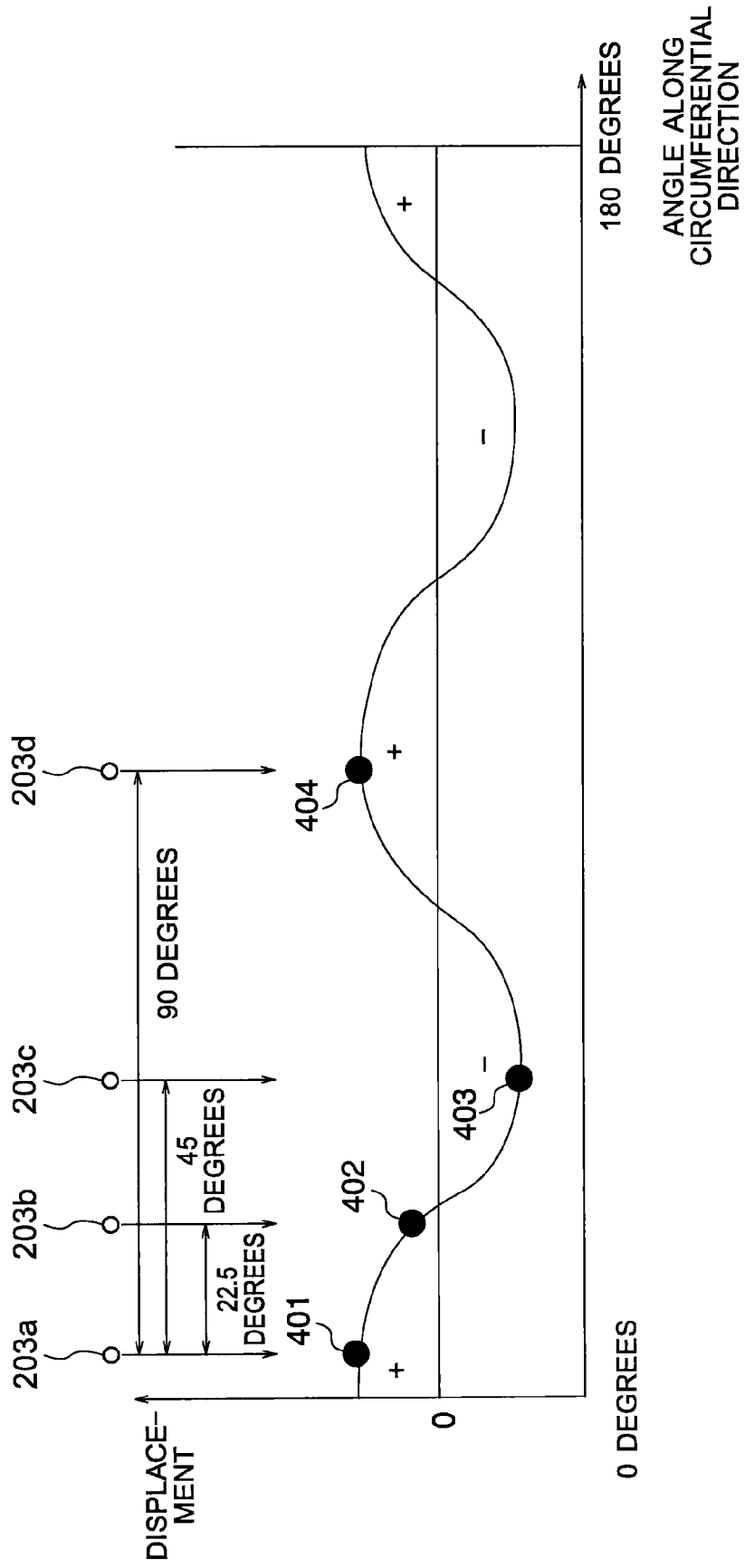
FIG. 29 is a graph indicating a displacement at the time of fourth-order resonant mode occurrence being capable of being measured by the blade vibration measuring apparatus according to the fourteenth embodiment.

In the fourth-order resonant mode indicated in FIG. 29, corresponding to the arrangement positions of the contactless displacement sensors 203a to 203d, displacements of the measurement points 401, 402 are at the plus side, a displacement of the measurement point 403 is at the minus side, and further, a displacement of the measurement point 404 is at the plus side.

Figure 30:
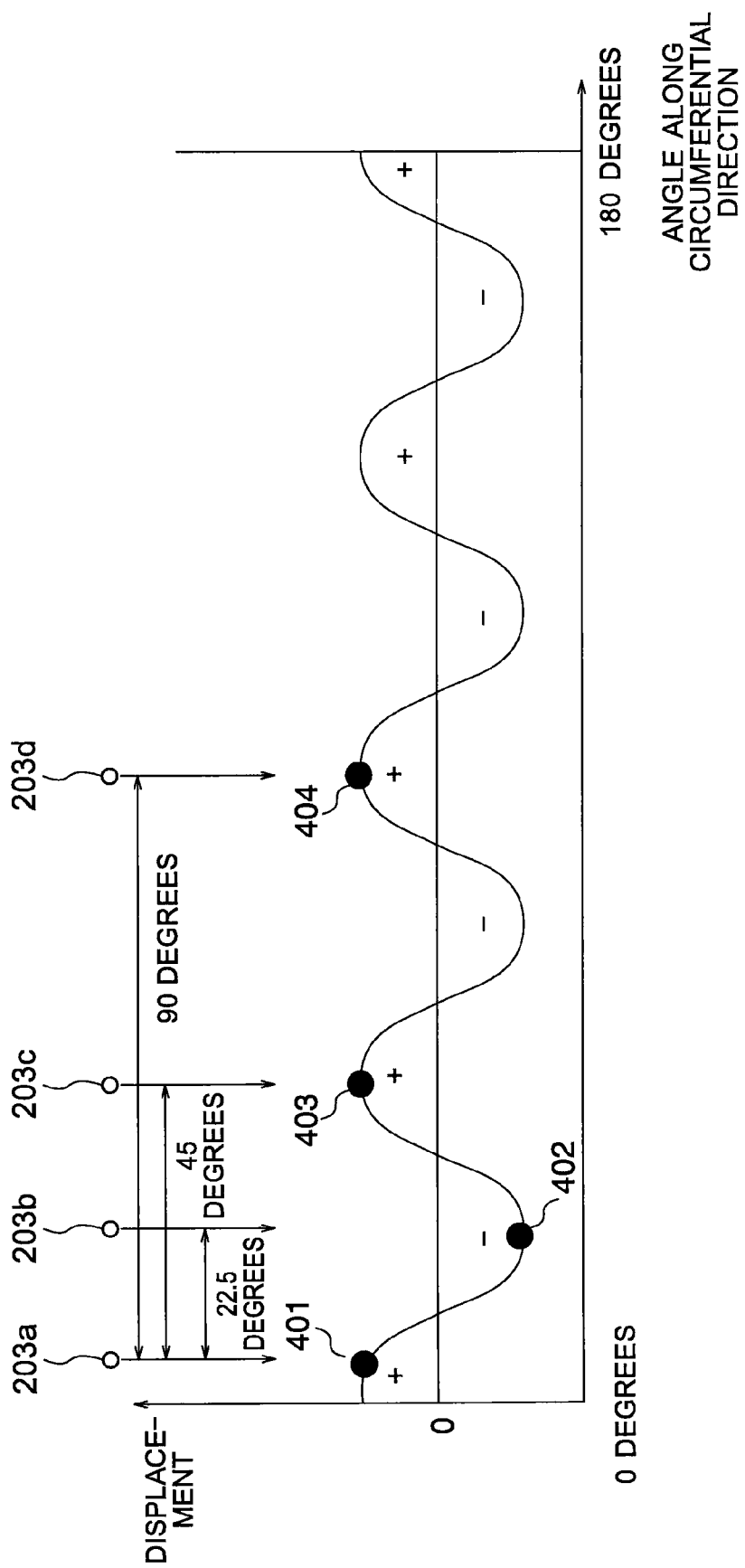
FIG. 30 is a graph indicating a displacement at the time of eighth-order resonant mode occurrence being capable of being measured by the blade vibration measuring apparatus according to the fourteenth embodiment.

In the eighth-order resonant mode indicated in FIG. 30, corresponding to the arrangement positions of the contactless displacement sensors 203a to 203d, a displacement of the measurement point 401 is at the plus side, a displacement of the measurement point 402 is at the minus side, a displacement of the measurement point 403 is at the plus side, and further, a displacement of the measurement point 404 is at the plus side.

In this manner, it is possible to easily determine which resonant mode occurs.

Here, to capture a resonant mode up to the eighth-order, the minimum interval of the arrangement of the contactless displacement sensors 203a to 203d is set to be 22.5°, that is, a half cycle of the eighth-order resonant mode. Owing to arrangement with the above intervals, a node in the eighth-order vibration mode can be captured invariably.

Further, owing to that the contactless displacement sensors are arranged at intervals being even multiples of the minimum interval as 22.5°, a node of a lower-order vibration mode can be captured.

According to the fourteenth embodiment, the resonant mode number can be effectively captured while reducing the number of the contactless displacement sensors compared to a case that the contactless displacement sensors are arranged at regular intervals in the circumferential direction. Accordingly, it is possible to contribute to cost reduction.

While certain embodiments have been described, these embodiments have been presented by way of example only, and are not intended to limit the scope of the inventions. Indeed, the novel systems (and methods) described herein may be embodied in a variety of other forms; furthermore, various omissions, substitutions and changes in the form of the systems (and 35 methods) described herein may be made without departing from the spirit of the inventions. The accompanying claims and their equivalents are intended to cover such forms or modifications as would within the scope and the spirit of the inventions.

What is claimed is:

1. A blade vibration measuring apparatus, comprising:
   a contactless displacement sensor which outputs a displacement measurement signal as measuring a displacement of a turbine moving blade in a rotation axis direction;
   a blade top position identifying device which outputs a blade top position identification signal to identify a top position based on a distance between the contactless displacement sensor and the top position of the turbine moving blade as receiving the displacement measurement signal output from the contactless displacement sensor; and
   a blade vibration calculating device which calculates a vibration amplitude and a vibration frequency of the turbine moving blade based on temporal variation of the distance between the contactless displacement sensor and the top position of the turbine moving blade as receiving the blade top position identification signal output from the blade top position identifying device.

2. The blade vibration measuring apparatus according to claim 1,
wherein a plurality of the contactless displacement sensors is arranged along a circumferential direction of the turbine moving blade;
pluralities of the blade top position identifying devices and the blade vibration calculating devices are arranged as corresponding to the respective contactless displacement sensors; and
a vibration mode identifying device which identifies a vibration mode number of the turbine moving blade based on the vibration amplitude and the vibration frequency of the turbine moving blade calculated by each of the blade vibration calculating devices is further provided.

3. The blade vibration measuring apparatus according to claim 1 with the contactless displacement sensor being solely arranged, further comprising:
a rotary jig which rotationally moves the contactless displacement sensor at the same radius along a circumferential direction of the turbine moving blade; and
a vibration mode identifying device which identifies a vibration mode number of the turbine moving blade based on the vibration amplitude and the vibration frequency of the turbine moving blade calculated by the blade vibration calculating device for each position of the contactless displacement sensor being rotationally moved by the rotary jig.

4. The blade vibration measuring apparatus according to claim 1, with a plurality of the contactless displacement sensors being arranged along a circumferential direction of the turbine moving blade, further comprising:
a rotary jig which rotationally moves the contactless displacement sensors respectively at the same radius along a circumferential direction of the turbine moving blade; and
a vibration mode identifying device which identifies a vibration mode number of the turbine moving blade based on the vibration amplitude and the vibration frequency of the turbine moving blade calculated by the blade vibration calculating device for each position of the plurality of contactless displacement sensors being rotationally moved by the rotary jig.

5. The blade vibration measuring apparatus according to claim 4,
wherein at least two of the plurality of contactless displacement sensors are arranged as being adjacent along the circumferential direction of the turbine moving blade; and
a displacement curve of the turbine moving blade in the rotation axis direction is capable of being specified based on the displacement measurement signals output from the at least two contactless displacement sensors.

6. The blade vibration measuring apparatus according to claim 1, further comprising:
a revolution speed adjusting device which varies revolution speed of the turbine moving blade; and
a resonant frequency detecting device which obtains a resonant frequency in a resonant state that the vibration amplitude of the turbine moving blade calculated by the blade vibration calculating device becomes maximal as the revolution speed of the turbine moving blade being varied by the revolution speed adjusting device.

7. The blade vibration measuring apparatus according to claim 6,
wherein the vibration amplitude calculated by the blade vibration calculating device when the turbine moving blade is rotated at predetermined revolution speed by the revolution speed adjusting device is memorized at the resonant frequency detecting device as reference vibration amplitude; and
a resonant frequency is obtained by the resonant frequency detecting device based on an amplitude difference value between the reference vibration amplitude and the vibration amplitude calculated by the blade vibration calculating device each time when the turbine moving blade is rotated by the revolution speed adjusting device at revolution speed being different from the predetermined revolution speed.

8. The blade vibration measuring apparatus according to claim 2, further comprising a revolution speed adjusting device which varies revolution speed of the turbine moving blade,
wherein the vibration mode identifying device identifies the vibration mode number in a resonant state of the turbine moving blade based on the vibration amplitude of the turbine moving blade calculated by each of the blade vibration calculating devices and the displacement of the turbine moving blade in the rotation axis direction detected by each of the contactless displacement sensors in the resonant state that the vibration amplitude of the turbine moving blade calculated by the blade vibration calculating devices becomes maximal as the revolution speed of the turbine moving blade being varied by the revolution speed adjusting device.

9. The blade vibration measuring apparatus according to claim 1, further comprising an angle adjusting device which adjusts a relative angle of the contactless displacement sensor against the turbine moving blade.

10. The blade vibration measuring apparatus according to claim 1, further comprising a distance adjusting device which adjusts a relative distance of the contactless displacement sensor against the turbine moving blade.

11. A blade vibration measuring apparatus comprising:
a plurality of contactless displacement sensors which is arranged along a circumferential direction of a turbine moving blade and which outputs displacement measurement signals as respectively measuring a displacement of the turbine moving blade in a rotation axis direction;
a plurality of blade top position identifying devices which is arranged as corresponding to the contactless displacement sensors and which outputs blade to position identification signals to identify a top position based on each distance between the contactless displacement sensors and the top position of the turbine moving blade as receiving the corresponding displacement measurement signals output from the contactless displacement sensors;
a plurality of blade vibration calculating devices which is arranged as corresponding to the blade top position identifying devices and which calculates a vibration amplitude and a vibration frequency of the turbine moving blade based on temporal variation of the distance from the contactless displacement sensors to the top position of the turbine moving blade as receiving the blade top position identification signals output from the blade top position identifying devices; and
a vibration mode identifying device which identifies a vibration mode number of the turbine moving blade based on the vibration amplitude and the vibration frequency of the turbine moving blade output from each of the blade vibration calculating devices,
wherein each of the blade top position identifying devices obtains a curve as performing curve fitting on displacements at a plurality of measurement points included in the received displacement measurement signal with mutual interpolation and identifies a top position of the turbine moving blade from a peak position of the curve.

12. The blade vibration measuring apparatus according to claim 11, further comprising a revolution speed adjusting device which varies revolution speed of the turbine moving blade,
wherein the vibration mode identifying device collects the blade top position identification signals identified by the blade top position identifying devices as sorting for each blade of the turbine moving blade and identifies a resonant mode number when a resonant phenomenon occurs at the turbine moving blade as revolution speed of the turbine moving blade being varied by the revolution speed adjusting device.

13. The blade vibration measuring apparatus according to claim 11,
wherein the plurality of contactless displacement sensors arranged along the circumferential direction of the turbine moving blade includes at least first, second, third, and fourth contactless displacement sensors;
the second contactless displacement sensor is arranged at a position having an interval against the first contactless displacement sensor by an amount of a half cycle of a predetermined-number-order resonant mode, the third contactless displacement sensor is arranged at a position having two-times of the interval against the first contactless displacement sensor, and the fourth contactless displacement sensor is arranged at a position having four-times of the interval against the first contactless displacement sensor.

14. A blade vibration measuring apparatus, comprising:
a revolution speed adjusting device which varies revolution speed of a turbine moving blade;
a rotational synchronization pulse generating device which outputs a rotational synchronization pulse each time when each blade of the turbine moving blade passes through a predetermined position;
a plurality of contactless displacement sensors which is arranged along a circumferential direction of the turbine moving blade and which outputs displacement measurement signals as respectively measuring a displacement of the turbine moving blade in a rotation axis direction at a time when the rotational synchronization pulse is provided;
a plurality of blade identical point measuring devices which is arranged as corresponding to the contactless displacement sensors and which outputs identical point displacement signals indicating respective distances between the contactless displacement sensors and identical points of the turbine moving blade corresponding to the rotational synchronization pulse as receiving the corresponding displacement measurement signals output from the contactless displacement sensors;
a blade reference sorting device which receives the identical point displacement signals output respectively from the blade identical point measuring devices and which outputs a chronological displacement signal sorted correspondingly for each blade of the turbine moving blade;
an FET calculating device which receives the chronological displacement signal output from the blade reference sorting device and which outputs a fast Fourier transform result signal as performing fast Fourier transform; and
a Campbell diagram creating device which receives the fast Fourier transform result signal output from the FET calculating device and which evaluates vibration characteristics of the turbine moving blade as creating a Campbell diagram.

15. The blade vibration measuring apparatus according to claim 1, further comprising an angle adjusting device which adjusts a relative angle of the contactless displacement sensor against the turbine moving blade, and a distance adjusting device which adjusts a relative distance of the contactless displacement sensor against the turbine moving blade.

* * * * *